United States Patent [19]

Malle et al.

[11] Patent Number: 5,931,973
[45] Date of Patent: Aug. 3, 1999

[54] 4,5-DIIMINOPYRAZOLINES, PROCESSES FOR THEIR PREPARATION, AND THEIR APPLICATION IN KERATIN FIBER DYEING COMPOSITIONS AND PROCESSES

[75] Inventors: Gérard Malle, Meaux; Laurent Vidal, Paris; Henri Samain, Bievres, all of France

[73] Assignee: L'Oreal, France

[21] Appl. No.: 08/828,295

[22] Filed: Mar. 21, 1997

[30] Foreign Application Priority Data

Mar. 21, 1996 [FR] France ................................. 96 03544

[51] Int. Cl.$^6$ ............................ A61K 7/13; C07D 231/10
[52] U.S. Cl. ........................ 8/431; 8/405; 8/568; 8/573; 8/575; 8/577; 546/275.4; 548/365.7; 548/367.4; 548/371.4; 548/372.5
[58] Field of Search ................................ 8/404, 405, 407, 8/409, 414, 415, 423, 425, 426, 431, 573, 568, 575, 577, 416; 548/367.4, 371.4, 372.5, 365.7; 546/275.4

[56] References Cited

U.S. PATENT DOCUMENTS

| | | | |
|---|---|---|---|
| 3,929,403 | 12/1975 | Kalopissis et al. | 8/416 |
| 3,956,342 | 5/1976 | Kalopissis et al. | 546/307 |
| 4,246,181 | 1/1981 | Kalopissis et al. | 8/405 |
| 4,675,130 | 6/1987 | Kalopissis et al. | 552/302 |
| 5,430,159 | 7/1995 | Neunhoeffer et al. | 548/371.4 |

FOREIGN PATENT DOCUMENTS

| | | |
|---|---|---|
| A-2050990 | 4/1971 | France . |
| WO-A-9408971 | 4/1994 | WIPO . |

OTHER PUBLICATIONS

Chemical Abstract, vol. 105, No. 7925a, Jul. 14, 1986, "Azomethine, azo and methine dyes of 5–hydroxy–5–hydroxy–5–amino– and 5–thiolo–3–methyl–1–phenyl–pyrazole."

Venkataraman, The Chemistry of Synthetic Dyes, vol. 1, Academic Press Inc., NY, p. 276, 1952 (no month available).

*Primary Examiner*—Caroline D. Liott
*Attorney, Agent, or Firm*—Finnegan, Henderson, Farabow, Garrett & Dunner

[57] ABSTRACT

Dyes selected from 4,5-diiminopyrazolines or their 4-ylideneamino-5-aminopyrazole tautomeric forms, a process for their preparation, and their use as direct dyes in dye compositions for keratin fibers, in particular for human keratin fibers. The dyes may also be used in lightening or non-lightening dye compositions for the direct dyeing of keratin fibers, and in dyeing processes using these compositions.

38 Claims, No Drawings

4,5-DIIMINOPYRAZOLINES, PROCESSES FOR THEIR PREPARATION, AND THEIR APPLICATION IN KERATIN FIBER DYEING COMPOSITIONS AND PROCESSES

The present invention relates to 4,5-diiminopyrazolines and to their 4-ylideneamino-5-aminopyrazole tautomeric forms, to a process for their preparation and their use as direct dyes in the dyeing of keratin fibres, in particular human keratin fibres, and especially the hair. More particularly, the present invention relates to lightening or non-lightening direct dye compositions containing these compounds.

It is known to dye keratin fibres, in particular the hair, with dye compositions containing either direct dyes, according to a so-called "direct dyeing" process, or oxidation dye precursors, according to a so-called "oxidation dyeing" process. The oxidation dyeing process involves one or more oxidation dye precursors, generally known as oxidation bases, such as ortho- or para-phenylenediamines and ortho- or para-aminophenols, which are colorless or weakly colored compounds and which, under the action of an oxidizing agent, give rise to colored compounds and dyes by a process of oxidative condensation. Couplers, also known as coloration modifiers, such as meta-phenylenediamines, meta-aminophenols and meta-diphenols, are usually combined with the oxidation bases in order to modify or enrich with glints the "foundation" colorations obtained by the condensation products of the oxidation bases. This oxidation dyeing process comprises applying to the keratin fibres a base or a mixture of a base and a coupler with an aqueous hydrogen peroxide solution as the oxidizing agent, allowing the mixture to remain of the fibres and then rinsing the fibres. The colorations which result are permanent, strong and resistant to external agents, in particular light, inclement weather, washing, perspiration and rubbing. This process, which is generally applied at basic pH, makes it possible to obtain dyeing and simultaneously lightening of the fibre, which is reflected in practice by the possibility of obtaining a final coloration which is lighter than the original color. In addition, lightening of the fibre has the advantageous effect of resulting in a uniform color in the case of grey hair and, in the case of naturally pigmented hair, of bringing the color out, i.e., making it more visible.

The process conventionally used in direct dyeing comprises applying to the keratin fibres direct dyes, or dyeing molecules, which have an affinity for the fibres, and leaving the dyes to stand on the fibres and then rinsing the fibres. The direct dyes that have been used to date are nitrobenzene dyes, anthraquinone dyes, nitropyridines, dyes of azo, xanthene, acridine or azine type and triarylmethane dyes.

The colorations which result are temporary or semi-permanent colorations because the nature of the interactions which bind the direct dyes to the keratin fibre and their desorption from the surface and/or from the core of the fibre result in low dyeing power and poor ability to withstand washing or perspiration. These direct dyes are also generally sensitive to the action of oxidizing agents such as an aqueous hydrogen peroxide solution, which makes them generally unusable in lightening direct dye compositions based on aqueous hydrogen peroxide solution and a basifying agent, which are similar to oxidation dyes.

These direct dyes also have a certain lack of stability to light associated with the low resistance of the chromophore to photochemical attack. In addition, their light-sensitivity is dependent on the distribution, uniform or as aggregates, of their molecules in the substrate.

Consequently there is a genuine need for direct dyes which make it possible to dye keratin fibres as strongly as oxidation dyes, which are as stable as the latter to light, which are also resistant to inclement weather, to washing and to perspiration, and which are also sufficiently stable in the presence of oxidizing agents such as an aqueous hydrogen peroxide solution to be able to obtain a simultaneous lightening of the fibre with the advantages outlined above.

After considerable research, Applicants have discovered a new family of direct dyes, 4,5-diiminopyrazolines and their 4-ylideneamino-5-aminopyrazole tautomeric forms, which make it possible to overcome the drawbacks of the direct dyes previously conventionally used, and lead to dyeings by direct dyeing, which are endowed with very good resistance to light, inclement weather, washing, perspiration and rubbing. Their good stability towards oxidizing agents such as aqueous hydrogen peroxide solution also allows them to be used in a lightening direct dyeing process.

This discovery forms the basis of the present invention.

A subject of the present invention is thus a dye composition comprising, in a medium which is suitable for dyeing, at least one 4,5-diiminopyrazoline compound of formula (I):

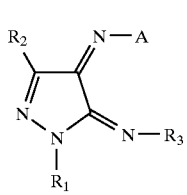

(I)

and/or its 4-ylideneamino-5-aminopyrazole tautomeric form of formula (II):

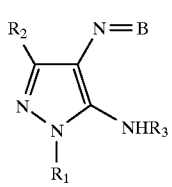

(II)

wherein, $R_1$ and $R_3$, which may be identical or different, represent a hydrogen atom; a $C_1$–$C_6$ alkyl radical; a $C_2$–$C_4$ hydroxyalkyl radical; a $C_2$–$C_4$ aminoalkyl radical; a phenyl radical; a phenyl radical substituted with a halogen atom or with a $C_1$–$C_4$ alkyl, $C_1$–$C_4$ alkoxy, nitro, trifluoromethyl, amino or $C_1$–$C_4$ alkylamino radical; a benzyl radical; a benzyl radical substituted with a halogen atom or with a $C_1$–$C_4$ alkyl, $C_1$–$C_4$ alkoxy, methylenedioxy or amino radical; or a radical:

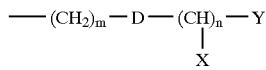

wherein m and n, which may be identical or different, represent an integer ranging from 1 to 3;
D represents oxygen or —NH—;
X represents hydrogen or $CH_3$;
Y represents $CH_3$ or $OR_4$, wherein $R_4$ represents hydrogen, methyl or ethyl;
and $R_3$ may also represent an amino radical;

R₂ represents a hydrogen atom; a $C_1$–$C_6$ alkyl radical; a $C_1$–$C_4$ hydroxyalkyl radical; a $C_1$–$C_4$ aminoalkyl radical; a $C_1$–$C_2$ alkylthio radical; a $C_1$–$C_5$ alkoxy radical; a trifluoromethyl, cyano or carboxyl radical; a phenyl radical; a phenyl radical substituted with a halogen atom or with a $C_1$–$C_4$ alkyl, $C_1$–$C_4$ alkoxy, nitro, trifluoromethyl, amino or $C_1$–$C_4$ alkylamino radical; a benzyl radical; a benzyl radical substituted with a halogen atom or with a $C_1$–$C_4$ alkyl, $C_1$–$C_4$ alkoxy, nitro, trifluoromethyl, amino or $C_1$–$C_4$ alkylamino radical; a heterocycle selected from thiophene, furan or pyridine; or a radical:

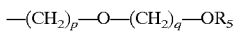

wherein p and q, which may be identical or different, are integers ranging from 1 to 3; and $R_5$ represents hydrogen or methyl;

A represents a radical:

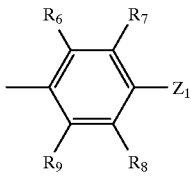

and

B represents, in formula (II), a radical:

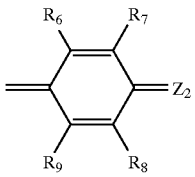

wherein:
$Z_1$ represents a hydroxyl radical; a $C_1$–$C_4$ alkoxy radical; an amino radical; an acetamido radical; a $C_1$–$C_4$ alkylamino radical; a $C_1$–$C_4$ hydroxyalkylamino radical; a $C_1$–$C_4$ aminoalkylamino radical; a radical $NR_{10}R_{11}$, wherein $R_{10}$ and $R_{11}$, which may be identical or different, represent a $C_1$–$C_4$ alkyl, $C_2$–$C_4$ hydroxyalkyl or $C_2$–$C_4$ aminoalkyl radical;

$R_6$, $R_7$, $R_8$ and $R_9$, which may each be identical or different, represent a hydrogen atom; a $C_1$–$C_4$ alkyl radical; a $C_1$–$C_4$ alkoxy radical; a $C_1$–$C_4$ alkylthio radical; an amino radical; a $C_1$–$C_4$ alkylamino radical; a carbamoylmethylamino radical; a $C_2$–$C_4$ hydroxyalkyl radical; a $C_2$–$C_4$ monohydroxyalkoxy radical; a $C_2$–$C_4$ dihydroxyalkoxy radical; a $C_1$–$C_2$ carboxyalkoxy radical; a chlorine, bromine or fluorine atom; a $C_1$–$C_2$ trifluoroalkyl radical;

a radical:

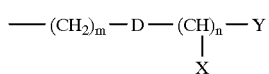

wherein m and n have the same meanings as defined above, and D, X and Y have the same meanings as defined above; or a radical $NR_{10}R_{11}$, wherein $R_{10}$ and $R_{11}$ have the same meanings as defined above;

$Z_2$ represents O or NR, wherein R represents hydrogen, or an acetyl, $C_1$–$C_4$ alkyl, $C_1$–$C_4$ hydroxyalkyl or $C_1$–$C_4$ aminoalkyl radial, it being understood that all the alkyl or alkoxy radicals of the groups defined above may be linear or branched.

During their use in dye formulations, the compounds of the invention correspond to one of the structures of formula (I) or of formula (II), or may, in certain cases, be converted from one structure to another according to a tautomeric equilibrium. This tautomeric equilibrium may or may not exist, depending on the nature of the radicals $Z_1$ or $Z_2$ in the formulae (I) and (II).

The compounds are preferably selected from
5-imino-4-[4'-(N,N-dimethylamino)phenyl] iminopyrazoline;
5-imino-4-[4'-(N,N-diethylamino)phenyl]iminopyrazoline;
5-imino-4-[(4'-hydroxy-2'-amino)phenyl]iminopyrazoline;
5-imino-4-[(2'-amino-4'-hydroxy-5'-methyl)phenyl] iminopyrazoline;
5-imino-4-[(2',4'-diamino-5'-methoxy)phenyl] iminopyrazoline;
5-imino-4-[(2'-(β-hydroxyethyl)amino-4'-hydroxy-5'-methyl)phenyl]iminopyrazoline;
5-imino-4-[(2',4'-diamino-5'-diamino-5'-(β-hydroxyethyloxy))phenyl]iminopyrazoline;
5-imino-4-[4'-(N,N-dimethylamino)phenyl]imino-1-methylpyrazoline;
5-imino-4-[4'-(N,N-dimethylamino)phenyl]imino-1-ethylpyrazoline;
5-imino-4-[4'-(N,N-dimethylamino)phenyl]imino-1-isopropylpyrazoline;
5-imino-4-[4'-(N,N-dimethylamino)phenyl]imino-1-phenylpyrazoline;
5-imino-4-[4'-(N,N-dimethylamino)phenyl]imino-1-tert-butylpyrazoline;
5-imino-4-[4'-(N,N-dimethylamino)phenyl]imino-1-(β-hydroxyethyl)pyrazoline;
5-imino-4-[4'-(N,N-dimethylamino)phenyl]imino-1-benzylpyrazoline;
5-imino-4-[4'-(N,N-diethylamino)phenyl]imino-1-methylpyrazoline;
5-imino-4-[4'-(N,N-diethylamino)phenyl]imino-1-ethylpyrazoline;
5-imino-4-[4'-(N,N-diethylamino)phenyl]imino-1-isopropylpyrazoline;
5-imino-4-[4'-(N,N-diethylamino)phenyl]imino-1-phenylpyrazoline;
5-imino-4-[4'-(N,N-diethylamino)phenyl]imino-1-tert-butylpyrazoline;
5-imino-4-[4'-(N,N-diethylamino)phenyl]imino-1-(β-hydroxyethyl)pyrazoline;
5-imino-4-[4'-(N,N-diethylamino)phenyl]imino-1-benzylpyrazoline;
5-imino-4-[(2'-amino-4'-hydroxy)phenyl]imino-1-methylpyrazoline;
5-imino-4-[(2'-amino-4'-hydroxy)phenyl]imino-1-ethylpyrazoline;
5-imino-4-[(2'-amino-4'-hydroxy)phenyl]imino-1-isopropylpyrazoline;
5-imino-4-[(2'-amino-4'-hydroxy)phenyl]imino-1-phenylpyrazoline;
5-imino-4-[(2'-amino-4'-hydroxy)phenyl]imino-1-benzylpyrazoline;
5-imino-4-[(2'-amino-4'-hydroxy)phenyl]imino-1-tert-butylpyrazoline;
5-imino-4-[(2'-amino-4'-hydroxy)phenyl]imino-1-(β-hydroxyethyl)pyrazoline;

5-imino-4-[(2'-amino-4'-hydroxy-5'-methyl)phenyl]imino-1-methylpyrazoline;
5-imino-4-[(2'-amino-4'-hydroxy-5'-methyl)phenyl]imino-1-ethylpyrazoline;
5-imino-4-[(2'-amino-4'-hydroxy-5'-methyl)phenyl]imino-1-isopropylpyrazoline;
5-imino-4-[(2'-amino-4'-hydroxy-5'-methyl)phenyl]imino-1-phenylpyrazoline;
5-imino-4-[(2'-amino-4'-hydroxy-5'-methyl)phenyl]imino-1-benzylpyrazoline;
5-imino-4-[(2'-amino-4'-hydroxy-5'-methyl)phenyl]imino-1-tert-butylpyrazoline;
5-imino-4-[(2'-amino-4'-hydroxy-5'-methyl)phenyl]imino-1-(β-hydroxyethyl)pyrazoline;
5-imino-4-[(2', 4'-diamino-5'-methoxy)phenyl]imino-1-methylpyrazoline;
5-imino-4-[(2',4'-diamino-5'-methoxy)phenyl]imino-1-ethylpyrazoline;
5-imino-4-[(2',4'-diamino-5'-methoxy)phenyl]imino-1-isopropylpyrazoline;
5-imino-4-[(2', 4'-diamino-5'-methoxy)phenyl]imino-1-phenylpyrazoline;
5-imino-4-[(2',4'-diamino-5'-methoxy)phenyl]imino-1-benzylpyrazoline;
5-imino-4-[(2',4'-diamino-5'-methoxy)phenyl]imino-1-tert-butylpyrazoline;
5-imino-4-[(2',4'-diamino-5'-methoxy)phenyl]imino-1-(β-hydroxyethyl)pyrazoline;
5-imino-4-[(2'-(β-hydroxyethyl)amino-4'-hydroxy-5'-methyl)phenyl]imino-1-methylpyrazoline;
5-imino-4-[(2'-(β-hydroxyethyl)amino-4'-hydroxy-5'-methyl)phenyl]imino-1-ethylpyrazoline;
5-imino-4-[(2'-(β-hydroxyethyl)amino-4'-hydroxy-5'-methyl)phenyl]imino-1-isopropylpyrazoline;
5-imino-4-[(2'-(β-hydroxyethyl)amino-4'-hydroxy-5'-methyl)phenyl]imino-1-tert-butylpyrazoline;
5-imino-4-[(2'-(β-hydroxyethyl)amino-4'-hydroxy-5'-methyl)phenyl]imino-1-phenylpyrazoline;
5-imino-4-[(2'-(β-hydroxyethyl)amino-4'-hydroxy-5'-methyl)phenyl]imino-1-benzylpyrazoline;
5-imino-4-[(2'-(β-hydroxyethyl)amino-4'-hydroxy-5'-methyl)phenyl]imino-1-(β-hydroxyethyl)pyrazoline;
5-imino-4-[(2',4'-diamino-5'-(β-hydroxyethyloxy))phenyl]imino-1-methylpyrazoline;
5-imino-4-[(2',4'-diamino-5'-(β-hydroxyethyloxy))phenyl]imino-1-ethylpyrazoline;
5-imino-4-[(2',4'-diamino-5'-(β-hydroxyethyloxy))phenyl]imino-1-isopropylpyrazoline;
5-imino-4-[(2',4'-diamino-5'-(β-hydroxyethyloxy))phenyl]imino-1-tert-butylpyrazoline;
5-imino-4-[(2',4'-diamino-5'-(β-hydroxyethyloxy))phenyl]imino-1-phenylpyrazoline;
5-imino-4-[(2',4'-diamino-5'-(β-hydroxyethyloxy))phenyl]imino-1-benzylpyrazoline;
5-imino-4-[(2',4'-diamino-5'-(β-hydroxyethyloxy))phenyl]imino-1-(β-hydroxyethyl)pyrazoline;
5-imino-4-[4'-(N,N-dimethylamino)phenyl]imino-3-methylpyrazoline;
5-imino-4-[4'-(N,N-dimethylamino)phenyl]imino-3-methyl-1-ethylpyrazoline;
5-imino-4-[4'-(N,N-dimethylamino)phenyl]imino-3-methyl-1-isopropylpyrazoline;
5-imino-4-[4'-(N,N-dimethylamino)phenyl]imino-3-methyl-1-tert-butylpyrazoline;
5-imino-4-[4'-(N,N-dimethylamino)phenyl]imino-3-methyl-1-phenylpyrazoline;
5-imino-4-[4'-(N,N-dimethylamino)phenyl]imino-3-methyl-1-benzylpyrazoline;
5-imino-4-[4'-(N,N-dimethylamino)phenyl]imino-3-methyl-1-(β-hydroxyethyl)pyrazoline;
5-imino-4-[4'-(N,N-dimethylamino)phenyl]imino-1,3-dimethylpyrazoline;
5-imino-4-[4'-(N,N-diethylamino)phenyl]imino-3-methylpyrazoline;
5-imino-4-[4'-(N,N-diethylamino)phenyl]imino-1,3-dimethylpyrazoline;
5-imino-4-[4'-(N,N-diethylamino)phenyl]imino-3-methyl-1-ethylpyrazoline;
5-imino-4-[4'-(N,N-diethylamino)phenyl]imino-3-methyl-1-isopropylpyrazoline;
5-imino-4-[4'-(N,N-diethylamino)phenyl]imino-3-methyl-1-tert-butylpyrazoline;
5-imino-4-[4'-(N,N-diethylamino)phenyl]imino-3-methyl-1-phenylpyrazoline;
5-imino-4-[4'-(N,N-diethylamino)phenyl]imino-3-methyl-1-benzylpyrazoline;
5-imino-4-[4'-(N,N-diethylamino)phenyl]imino-3-methyl-1-(β-hydroxyethyl)pyrazoline;
5-imino-4-[(2'-amino-4'-hydroxy)phenyl]imino-3-methylpyrazoline;
5-imino-4-[(2'-amino-4'-hydroxy)phenyl]imino-1,3-dimethylpyrazoline;
5-imino-4-[(2'-amino-4'-hydroxy)phenyl]imino-3-methyl-1-ethylpyrazoline;
5-imino-4-[(2'-amino-4'-hydroxy)phenyl]imino-3-methyl-1-isopropylpyrazoline;
5-imino-4-[(2'-amino-4'-hydroxy)phenyl]imino-3-methyl-1-tert-butylpyrazoline;
5-imino-4-[(2'-amino-4'-hydroxy)phenyl]imino-3-methyl-1-phenylpyrazoline;
5-imino-4-[(2'-amino-4'-hydroxy)phenyl]imino-3-methyl-1-benzylpyrazoline;
5-imino-4-[(4'-amino-4'-hydroxy)phenyl]imino-3-methyl-1-(β-hydroxyethyl)pyrazoline;
5-imino-4-[(2'-amino-4'-hydroxy-5'-methyl)phenyl]imino-3-methylpyrazoline;
5-imino-4-[(2'-amino-4'-hydroxy-5'-methyl)phenyl]imino-1,3-dimethylpyrazoline;
5-imino-4-[(2'-amino-4'-hydroxy-5'-methyl)phenyl]imino-3-methyl-1-ethylpyrazoline;
5-imino-4-[(2'-amino-4'-hydroxy-5'-methyl)phenyl]imino-3-methyl-1-isopropylpyrazoline;
5-imino-4-[(2'-amino-4'-hydroxy-5'-methyl)phenyl]imino-3-methyl-1-tert-butylpyrazoline;
5-imino-4-[(2'-amino-4'-hydroxy-5'-methyl)phenyl]imino-3-methyl-1-phenylpyrazoline;
5-imino-4-[(2'-amino-4'-hydroxy-5'-methyl)phenyl]imino-3-methyl-1-benzylpyrazoline;
5-imino-4-[(2'-amino-4'-hydroxy-5'-methyl)phenyl]imino-3-methyl-1-(β-hydroxyethyl)pyrazoline;
5-imino-4-[(2',4'-diamino-5'-methoxy)phenyl]imino-3-methylpyrazoline;
5-imino-4-[(2',4'-diamino-5'-methoxy)phenyl]imino-1,3-dimethylpyrazoline;
5-imino-4-[(2',4'-diamino-5'-methoxy)phenyl]imino-3-methyl-1-ethylpyrazoline;
5-imino-4-[(2',4'-diamino-5'-methoxy)phenyl]imino-3-methyl-1-isopropylpyrazoline;
5-imino-4-[(2',4'-diamino-5'-methoxy)phenyl]imino-3-methyl-1-tert-butylpyrazoline;
5-imino-4-[(2',4'-diamino-5'-methoxy)phenyl]imino-3-methyl-1-phenylpyrazoline;
5-imino-4-[(2',4'-diamino-5'-methoxy)phenyl]imino-3-methyl-1-benzyipyrazoline;
5-imino-4-[(2',4'-diamino-5'-methoxy)phenyl]imino-3-methyl-1-(β-hydroxyethyl)pyrazoline;

5-imino-4-[(2'-(β-hydroxyethyl)amino-4'-hydroxy-5'-methyl)phenyl]imino-3-methylpyrazoline;

5-imino-4-[(2'-(β-hydroxyethyl)amino-4'-hydroxy-5'-methyl)phenyl]imino-1,3-dimethylpyrazoline;

5-imino-4-[(2'-(β-hydroxyethyl)amino-4'-hydroxy-5'-methyl)phenyl]imino-3-methyl-1-ethylpyrazoline;

5-imino-4-[(2'-(β-hydroxyethyl)amino-4'-hydroxy-5'-methyl)phenyl]imino-3-methyl-1-isopropylpyrazoline;

5-imino-4-[(2'-(β-hydroxyethyl)amino-4'-hydroxy-5'-methyl)phenyl]imino-3-methyl-1-tert-butylpyrazoline;

5-imino-4-[(2'-(β-hydroxyethyl)amino-4'-hydroxy-5'-methyl)phenyl]imino-3-methyl-1-phenylpyrazoline;

5-imino-4-[(2'-(β-hydroxyethyl)amino-4'-hydroxy-5'-methyl)phenyl]imino-3-methyl-1-benzylpyrazoline;

5-imino-4-[(2'-(β-hydroxyethyl)amino-4'-hydroxy-5'-methyl)phenyl]imino-3-methyl-1-(β-hydroxyethyl)pyrazoline;

5-imino-4-[(2',4'-diamino-5'-(β-hydroxyethyloxy))phenyl]imino-3-methylpyrazoline;

5-imino-4-[(2',4'-diamino-5'-(β-hydroxyethyloxy))phenyl]imino-1,3-dimethylpyrazoline;

5-imino-4-[(2',4'-diamino-5'-(β-hydroxyethyloxy))phenyl]imino-3-methyl-1-ethylpyrazoline;

5-imino-4-[(2',4'-diamino-5'-(β-hydroxyethyloxy))phenyl]imino-3-methyl-1-isopropylpyrazoline;

5-imino-4-[(2',4'-diamino-5'-(β-hydroxyethyloxy))phenyl]imino-3-methyl-1-tert-butylpyrazoline;

5-imino-4-[(2',4'-diamino-5'-(β-hydroxyethyloxy))phenyl]imino-3-methyl-1-phenylpyrazoline;

5-imino-4-[(2',4'-diamino-5'-(β-hydroxyethyloxy))phenyl]imino-3-methyl-1-benzylpyrazoline;

5-imino-4-[(2',4'-diamino-5'-(β-hydroxyethyloxy))phenyl]imino-3-methyl-1-(β-hydroxyethyl)pyrazoline;

3-hydroxymethyl-5-imino-4-[4'-(N,N-dimethylamino)phenyl]iminopyrazoline;

3-hydroxymethyl-5-imino-4-[4'-(N,N-dimethylamino)phenyl]imino-1-methylpyrazoline;

3-hydroxymethyl-5-imino-4-[4'-(N,N-dimethylamino)phenyl]imino-1-ethylpyrazoline;

3-hydroxymethyl-5-imino-4-[4'-(N,N-dimethylamino)phenyl]imino-1-isopropylpyrazoline;

3-hydroxymethyl-5-imino-4-[4'-(N,N-dimethylamino)phenyl]imino-1-tert-butylpyrazoline;

3-hydroxymethyl-5-imino-4-[4'-(N,N-dimethylamino)phenyl]imino-1-phenylpyrazoline;

3-hydroxymethyl-5-imino-4-[4'-(N,N-dimethylamino)phenyl]imino-1-benzylpyrazoline;

3-hydroxymethyl-5-imino-4-[4'-(N,N-dimethylamino)phenyl]imino-1-(β-hydroxyethyl)pyrazoline;

3-hydroxymethyl-5-imino-4-[4'-(N,N-diethylamino)phenyl]iminopyrazoline;

3-hydroxymethyl-5-imino-4-[4'-(N,N-diethylamino)phenyl]imino-1-methylpyrazoline;

3-hydroxymethyl-5-imino-4-[4'-(N,N-diethylamino)phenyl]imino-1-ethylpyrazoline;

3-hydroxymethyl-5-imino-4-[4'-(N,N-diethylamino)phenyl]imino-1-isopropylpyrazoline;

3-hydroxymethyl-5-imino-4-[4'-(N,N-diethylamino)phenyl]imino-1-tert-butylpyrazoline;

3-hydroxymethyl-5-imino-4-[4'-(N,N-diethylamino)phenyl]imino-1-phenylpyrazoline;

3-hydroxymethyl-5-imino-4-[4'-(N,N-diethylamino)phenyl]imino-1-benzylpyrazoline;

3-hydroxymethyl-5-imino-4-[4'-(N,N-diethylamino)phenyl]imino-1-(β-hydroxyethyl)pyrazoline;

3-hydroxymethyl-5-imino-4-[(2'-amino-4'-hydroxy)phenyl]iminopyrazoline;

3-hydroxymethyl-5-imino-4-[(2'-amino-4'-hydroxy)phenyl]imino-1-methylpyrazoline;

3-hydroxymethyl-5-imino-4-[(2'-amino-4'-hydroxy)phenyl]imino-1-ethylpyrazoline;

3-hydroxymethyl-5-imino-4-[(2'-amino-4'-hydroxy)phenyl]imino-1-isopropylpyrazoline;

3-hydroxymethyl-5-imino-4-[(2'-amino-4'-hydroxy)phenyl]imino-1-tert-butylpyrazoline;

3-hydroxymethyl-5-imino-4-[(2'-amino-4'-hydroxy)phenyl]imino-1-phenylpyrazoline;

3-hydroxymethyl-5-imino-4-[(2'-amino-4'-hydroxy)phenyl]imino-1-benzylpyrazoline;

3-hydroxymethyl-5-imino-4-[(2'-amino-4'-hydroxy)phenyl]imino-1-(β-hydroxyethyl)pyrazoline;

3-hydroxymethyl-5-imino-4-[(2'-amino-4'-hydroxy-5'-methyl)phenyl]iminopyrazoline;

3-hydroxymethyl-5-imino-4-[(2'-amino-4'-hydroxy-5'-methyl)phenyl]imino-1-methylpyrazoline;

3-hydroxymethyl-5-imino-4-[(2'-amino-4'-hydroxy-5'-methyl)phenyl]imino-1-ethylpyrazoline;

3-hydroxymethyl-5-imino-4-[(2'-amino-4'-hydroxy-5'-methyl)phenyl]imino-1-isopropylpyrazoline;

3-hydroxymethyl-5-imino-4-[(2'-amino-4'-hydroxy-5'-methyl)phenyl]imino-1-tert-butylpyrazoline;

3-hydroxymethyl-5-imino-4-[(2'-amino-4'-hydroxy-5'-methyl)phenyl]imino-1-phenylpyrazoline;

3-hydroxymethyl-5-imino-4-[(2'-amino-4'-hydroxy-5'-methyl)phenyl]imino-1-benzylpyrazoline;

3-hydroxymethyl-5-imino-4-[(2'-amino-4'-hydroxy-5'-methyl)phenyl]imino-1-(β-hydroxyethyl)pyrazoline;

3-hydroxymethyl-5-imino-4-[(2',4'-diamino-5'-methoxy)phenyl]iminopyrazoline;

3-hydroxymethyl-5-imino-4-[(2',4'-diamino-5'-methoxy)phenyl]imino-1-methylpyrazoline;

3-hydroxymethyl-5-imino-4-[(2',4'-diamino-5'-methoxy)phenyl]imino-1-ethylpyrazoline;

3-hydroxymethyl-5-imino-4-[(2',4'-diamino-5'-methoxy)phenyl]imino-1-isopropylpyrazoline;

3-hydroxymethyl-5-imino-4-[(2',4'-diamino-5'-methoxy)phenyl]imino-1-tert-butylpyrazoline;

3-hydroxymethyl-5-imino-4-[(2',4'-diamino-5'-methoxy)phenyl]imino-1-phenylpyrazoline;

3-hydroxymethyl-5-imino-4-[(2', 4'-diamino-5'-methoxy)phenyl]imino-1-benzylpyrazoline;

3-hydroxymethyl-5-imino-4-[(2', 4'-diamino-5'-methoxy)phenyl]imino-1-(β-hydroxyethyl)pyrazoline;

3-hydroxymethyl-5-imino-4-[(2', 4'-diamino-5'-(β-hydroxyethyloxy))phenyl]iminopyrazoline;

3-hydroxymethyl-5-imino-4-[(2', 4'-diamino-5'-(β-hydroxyethyloxy))phenyl]imino-1-methylpyrazoline;

3-hydroxymethyl-5-imino-4-[(2', 4'-diamino-5'-(β-hydroxyethyloxy))phenyl]imino-1-ethylpyrazoline;

3-hydroxymethyl-5-imino-4-[(2', 4'-diamino-5'-(β-hydroxyethyloxy))phenyl]imino-1-isopropylpyrazoline;

3-hydroxymethyl-5-imino-4-[(2', 4'-diamino-5'-(β-hydroxyethyloxy))phenyl]imino-1-tert-butylpyrazoline;

3-hydroxymethyl-5-imino-4-[(2', 4'-diamino-5'-(β-hydroxyethyloxy))phenyl]imino-1-phenylpyrazoline;

3-hydroxymethyl-5-imino-4-[(2',4'-diamino-5'-(β-hydroxyethyloxy))phenyl]imino-1-benzylpyrazoline;

3-hydroxymethyl-5-imino-4-[(2', 4'-diamino-5'-(β-hydroxyethyloxy))phenyl]imino-1-(β-hydroxyethyl)pyrazoline;

3-hydroxymethyl-5-imino-4-[(2'-(β-hydroxyethyl)amino-4'-hydroxy-5'-methyl)phenyl]iminopyrazoline;

3-hydroxymethyl-5-imino-4-[(2'-(β-hydroxyethyl)amino-4'-hydroxy-5'-methyl)phenyl]imino-1-methylpyrazoline;

3-hydroxymethyl-5-imino-4-[(2'-(β-hydroxyethyl)amino-4'-hydroxy-5'-methyl)phenyl]imino-1-ethylpyrazoline;
3-hydroxymethyl-5-imino-4-[(2'-(β-hydroxyethyl)amino-4'-hydroxy-5'-methyl)phenyl]imino-1-isopropylpyrazoline;
3-hydroxymethyl-5-imino-4-[(2'-(β-hydroxyethyl)amino-4'-hydroxy-5'-methyl)phenyl]imino-1-tert-butylpyrazoline;
3-hydroxymethyl-5-imino-4-[(2'-(β-hydroxyethyl)amino-4'-hydroxy-5'-methyl)phenyl]imino-1-phenylpyrazoline;
3-hydroxymethyl-5-imino-4-[(2'-(β-hydroxyethyl)amino-4'-hydroxy-5'-methyl)phenyl]imino-1-benzylpyrazoline;
3-hydroxymethyl-5-imino-4-[(2'-(β-hydroxyethyl)amino-4'-hydroxy-5'-methyl)phenyl]imino-1-(β-hydroxyethyl)pyrazoline;
3-trifluoromethyl-5-imino-4-[4'-(N,N-dimethylamino)phenyl]iminopyrazoline;
3-trifluoromethyl-5-imino-4-[4'-(N,N-dimethylamino)phenyl]imino-1-methylpyrazoline
3-trifluoromethyl-5-imino-4-[4'-(N,N-dimethylamino)phenyl]imino-1-ethylpyrazoline;
3-trifluoromethyl-5-imino-4-[4'-(N,N-dimethylamino)phenyl]imino-1-isopropylpyrazoline;
3-trifluoromethyl-5-imino-4-[4'-(N,N-dimethylamino)phenyl]imino-1-tert-butylpyrazoline;
3-trifluoromethyl-5-imino-4-[4'-(N,N-dimethylamino)phenyl]imino-1-phenylpyrazoline;
3-trifluoromethyl-5-imino-4-[4'-(N,N-dimethylamino)phenyl]imino-1-benzylpyrazoline;
3-trifluoromethyl-5-imino-4-[4'-(N,N-dimethylamino)phenyl]imino-1-(β-hydroxyethyl)pyrazoline;
3-trifluoromethyl-5-imino-4-[4'-(N,N-diethylamino)phenyl]iminopyrazoline;
3-trifluoromethyl-5-imino-4-[4'-(N,N-diethylamino)phenyl]imino-1-methylpyrazoline;
3-trifluoromethyl-5-imino-4-[4'-(N,N-diethylamino)phenyl]imino-1-ethylpyrazoline;
3-trifluoromethyl-5-imino-4-[4'-(N,N-diethylamino)phenyl]imino-1-isopropylpyrazoline;
3-trifluoromethyl-5-imino-4-[4'-(N,N-diethylamino)phenyl]imino-1-tert-butylpyrazoline;
3-trifluoromethyl-5-imino-4-[4'-(N,N-diethylamino)phenyl]imino-1-phenylpyrazoline;
3-trifluoromethyl-5-imino-4-[4'-(N,N-diethylamino)phenyl]imino-1-benzylpyrazoline;
3-trifluoromethyl-5-imino-4-[4'-(N,N-diethylamino)phenyl]imino-1-(β-hydroxyethyl)pyrazoline;
3-trifluoromethyl-5-imino-4-[(2'-amino-4'-hydroxy)phenyl]iminopyrazoline;
3-trifluoromethyl-5-imino-4-[(2'-amino-4'-hydroxy)phenyl]imino-1-methylpyrazoline;
3-trifluoromethyl-5-imino-4-[(2'-amino-4'-hydroxy)phenyl]imino-1-ethylpyrazoline;
3-trifluoromethyl-5-imino-4-[(2'-amino-4'-hydroxy)phenyl]imino-1-isopropylpyrazoline;
3-trifluoromethyl-5-imino-4-[(2'-amino-4'-hydroxy)phenyi]imino-1-tert-butylpyrazoline;
3-trifluoromethyl-5-imino-4-[(2'-amino-4'-hydroxy)phenyl]imino-1-phenylpyrazoline;
3-trifluoromethyl-5-imino-4-[(2'-amino-4'-hydroxy)phenyl]imino-1-benzylpyrazoline;
3-trifluoromethyl-5-imino-4-[(2'-amino-4'-hydroxy)phenyl]imino-1-(β-hydroxyethyl)pyrazoline;
3-trifluoromethyl-5-imino-4-[(2'-amino-4'-hydroxy-5'-methyl)phenyl]iminopyrazoline;
3-trifluoromethyl-5-imino-4-[(2'-amino-4'-hydroxy-5'-methyl)phenyl]imino1-methylpyrazoline;
3-trifluoromethyl-5-imino-4-[(2'-amino-4'-hydroxy-5'-methyl)phenyl]imino-1-ethylpyrazoline;
3-trifluoromethyl-5-imino-4-[(2'-amino-4'-hydroxy-5'-methyl)phenyl]imino-1-isopropylpyrazoline;
3-trifluoromethyl-5-imino-4-[(2'-amino-4'-hydroxy-5'-methyl)phenyl]imino-1-tert-butylpyrazoline;
3-trifluoromethyl-5-imino-4-[(2'-amino-4'-hydroxy-5'-methyl)phenyl]imino-1-phenylpyrazoline;
3-trifluoromethyl-5-imino-4-[(2'-amino-4'-hydroxy-5'-methyl)phenyl]imino-1-benzylpyrazoline;
3-trifluoromethyl-5-imino-4-[(2'-amino-4'-hydroxy-5'-methyl)phenyl]imino-1-(β-hydroxyethyl)pyrazoline;
3-trifluoromethyl-5-imino-4-[(2',4'-diamino-5'-methoxy)phenyl]iminopyrazoline;
3-trifluoromethyl-5-imino-4-[(2',4'-diamino-5'-methoxy)phenyl]imino-1-methylpyrazoline;
3-trifluoromethyl-5-imino-4-[(2',4'-diamino-5'-methoxy)phenyl]imino-1-ethylpyrazoline;
3-trifluoromethyl-5-imino-4-[(2',4'-diamino-5'-methoxy)phenyl]imino-1-isopropylpyrazoline;
3-trifluoromethyl-5-imino-4-[(2',4'-diamino-5'-methoxy)phenyl]imino-1-tert-butylpyrazoline;
3-trifluoromethyl-5-imino-4-[(2',4'-diamino-5'-methoxy)phenyl]imino-1-phenylpyrazoline;
3-trifluoromethyl-5-imino-4-[(2',4'-diamino-5'-methoxy)phenyl]imino-1-benzylpyrazoline;
3-trifluoromethyl-5-imino-4-[(2',4'-diamino-5'-methoxy)phenyl]imino-1-(β-hydroxyethyl)pyrazoline;
3-trifluoromethyl-5-imino-4-[(2',4'-diamino-5'-(β-hydroxyethyloxy))phenyl]-iminopyrazoline;
3-trifluoromethyl-5-imino-4-[(2',4'-diamino-5'-(β-hydroxyethyloxy))phenyl]imino-1-methylpyrazoline;
3-trifluoromethyl-5-imino-4-[(2', 4'-diamino-5'-(β-hydroxyethyloxy))phenyl]imino-1-ethylpyrazoline;
3-trifluoromethyl-5-imino-4-[(2', 4'-diamino-5'-(β-hydroxyethyloxy))phenyl]imino-1-isopropylpyrazoline;
3-trifluoromethyl-5-imino-4-[(2', 4'-diamino-5'-(β-hydroxyethyloxy))phenyl]imino-1-tert-butylpyrazoline;
3-trifluoromethyl-5-imino-4-[(2', 4'-diamino-5'-(β-hydroxyethyloxy))phenyl]imino-1-phenylpyrazoline;
3-trifluoromethyl-5-imino-4-[(2', 4'-diamino-5'-(β-hydroxyethyloxy))phenyl]imino-1-benzylpyrazoline;
3-trifluoromethyl-5-imino-4-[(2',4'-diamino-5'-(β-hydroxyethyloxy))phenyl]imino-1-(βhydroxyethyl)pyrazoline;
3-trifluoromethyl-5-imino-4-[(2'-(β-hydroxyethyl)amino-4'-hydroxy-5'-methyl)phenyl]iminopyrazoline;
3-trifluoromethyl-5-imino-4-[(2'-(β-hydroxyethyl)amino-4'-hydroxy-5'-methyl)phenyl]imino-1-methylpyrazoline;
3-trifluoromethyl-5-imino-4-[(2'-(β-hydroxyethyl)amino-4'-hydroxy-5'-methyl)phenyl]imino-1-ethylpyrazoline;
3-trifluoromethyl-5-imino-4-[(2'-(β-hydroxyethyl)amino-4'-hydroxy-5'-methyl)phenyl]imino-1-isopropylpyrazoline;
3-trifluoromethyl-5-imino-4-[(2'-(β-hydroxyethyl)amino-4'-hydroxy-5'-methyl)phenyl]imino-1-tert-butylpyrazoline;
3-trifluoromethyl-5-imino-4-[(2'-(β-hydroxyethyl)amino-4'-hydroxy-5'-methyl)phenyl]imino-1-phenylpyrazoline;
3-trifluoromethyl-5-imino-4-[(2'-(β-hydroxyethyl)amino-4'-hydroxy-5'-methyl)phenyl]imino-1-benzylpyrazoline;
3-trifluoromethyl-5-imino-4-[(2'-(β-hydroxyethyl)amino-4'-hydroxy-5'-methyl)phenyl]imino-1-(β-hydroxyethyl)pyrazolin;
3-dimethylamino-5-imino-4-[4'-(N,N-dimethylamino)phenyl]iminopyrazoline;
3-dimethylamino-5-imino-4-[4'-(N,N-dimethylamino)phenyl]imino-1-methylpyrazoline;

3-dimethylamino-5-imino-4-[4'-(N,N-dimethylamino)
 phenyl]imino-1-ethylpyrazoline;
3-dimethylamino-5-imino-4-[4'-(N,N-dimethylamino)
 phenyl]imino-1-isopropylpyrazoline;
3-dimethylamino-5-imino-4-[4'-(N,N-dimethylamino)
 phenyl]imino-1-tert-butylpyrazoline;
3-dimethylamino-5-imino-4-[4'-(N,N-dimethylamino)
 phenyl]imino-1-phenylpyrazoline;
3-dimethylamino-5-imino-4-[4'-(N,N-dimethylamino)
 phenyl]imino-1-benzylpyrazoline;
3-dimethylamino-5-imino-4-[4'-(N,N-dimethylamino)
 phenyl]imino-1-(β-hydroxyethyl)pyrazoline;
3-dimethylamino-5-imino-4-[4'-(N,N-diethylamino)phenyl]
 iminopyrazoline;
3-dimethylamino-5-imino-4-[4'-(N,N-diethylamino)phenyl]
 imino-1-methylpyrazoline;
3-dimethylamino-5-imino-4-[4'-(N,N-diethylamino)phenyl]
 imino-1-ethylpyrazoline;
3-dimethylamino-5-imino-4-[4'-(N,N-diethylamino)phenyl]
 imino-1-isopropylpyrazoline;
3-dimethylamino-5-imino-4-[4'-(N,N-diethylamino)phenyl]
 imino-1-tert-butylpyrazoline;
3-dimethylamino-5-imino-4-[4'-(N,N-diethylamino)phenyl]
 imino-1-phenylpyrazoline;
3-dimethylamino-5-imino-4-[4'-(N,N-diethylamino)phenyl]
 imino-1-benzylpyrazoline;
3-dimethylamino-5-imino-4-[4'-(N,N-diethylamino)phenyl]
 imino-1-(β-hydroxyethyl)pyrazoline;
3-dimethylaminomethyl-5-imino-4-[(4'-hydroxy-2'-amino)
 phenyl]iminopyrazoline;
3-dimethylaminomethyl-5-imino-4-[(4'-hydroxy-2'-amino)
 phenyl]imino-1-methylpyrazoline;
3-dimethylaminomethyl-5-imino-4-[(4'-hydroxy-2'-amino)
 phenyl]imino-1-ethylpyrazoline;
3-dimethylaminomethyl-5-imino-4-[(4'-hydroxy-2'-amino)
 phenyl]imino-1-isopropylpyrazoline;
3-dimethylaminomethyl-5-imino-4-[(4'-hydroxy-2'-amino)
 phenyl]imino-1-tert-butylpyrazoline;
3-dimethylaminomethyl-5-imino-4-[(4'-hydroxy-2'-amino)
 phenyl]imino-1-phenylpyrazoline;
3-dimethylaminomethyl-5-imino-4-[(4'-hydroxy-2'-amino)
 phenyl]imino-1-benzylpyrazoline;
3-dimethylaminomethyl-5-imino-4-[(4'-hydroxy-2'-amino)
 phenyl]imino-1-(β-hydroxyethyl)pyrazoline;
3-dimethylaminomethyl-5-imino-4-[(2'-amino-4'-hydroxy-
 5'-methyl)phenyl]iminopyrazoline;
3-dimethylaminomethyl-5-imino-4-[(2'-amino-4'-hydroxy-
 5'-methyl)phenyl]imino-1-methylpyrazoline;
3-dimethylaminomethyl-5-imino-4-[(2'-amino-4'-hydroxy-
 5'-methyl)phenyl]imino-1-ethylpyrazoline;
3-dimethylaminomethyl-5-imino-4-[(2'-amino-4'-hydroxy-
 5'-methyl)phenyl]imino-1-isopropylpyrazoline;
3-dimethylaminomethyl-5-imino-4-[(2'-amino-4'-hydroxy-
 5'-methyl)phenyl]imino-1-tert-butylpyrazoline;
3-dimethylaminomethyl-5-imino-4-[(2'-amino-4'-hydroxy-
 5'-methyl)phenyl]imino-1-phenylpyrazoline;
3-dimethylaminomethyl-5-imino-4-[(2'-amino-4'-hydroxy-
 5'-methyl)phenyl]imino-1-benzylpyrazoline;
3-dimethylaminomethyl-5-imino-4-[(2'-amino-4'-hydroxy-
 5'-methyl)phenyl]imino-1-(β-hydroxyethyl)pyrazoline;
3-dimethylaminomethyl-5-imino-4-[(2',4'-diamino-5'-
 methoxy)phenyl]iminopyrazoline;
3-dimethylaminomethyl-5-imino-4-[(2',4'-diamino-5'-
 methoxy)phenyl]imino-1-methylpyrazoline;
3-dimethylaminomethyl-5-imino-4-[(2',4'-diamino-5'-
 methoxy)phenyl]imino-1-ethylpyrazoline;
3-dimethylaminomethyl-5-imino-4-[(2',4'-diamino-5'-
 methoxy)phenyl]imino-1-isopropylpyrazoline;
3-dimethylaminomethyl-5-imino-4-[(2',4'-diamino-5'-
 methoxy)phenyl]imino-1-tert-butylpyrazoline;
3-dimethylaminomethyl-5-imino-4-[(2',4'-diamino-5'-
 methoxy)phenyl]imino-1-phenylpyrazoline;
3-dimethylaminomethyl-5-imino-4-[(2',4'-diamino-5'-
 methoxy)phenyl]imino-1-benzylpyrazoline;
3-dimethylaminomethyl-5-imino-4-[(2',4'-diamino-5'-
 methoxy)phenyl]imino-1-(β-hydroxyethyl)pyrazoline;
3-dimethylaminomethyl-5-imino-4-[(2'-(β-hydroxyethyl)
 amino-4'-hydroxy-5'-methyl)phenyl]iminopyrazoline;
3-dimethylaminomethyl-5-imino-4-[(2'-(β-hydroxyethyl)
 amino-4'-hydroxy-5'-methyl)phenyl]imino-1-
 methylpyrazoline;
3-dimethylaminomethyl-5-imino-4-[(2'-(β-hydroxyethyl)
 amino-4'-hydroxy-5'-methyl)phenyl]imino-1-
 ethylpyrazoline;
3-dimethylaminomethyl-5-imino-4-[(2'-(β-hydroxyethyl)
 amino-4'-hydroxy-5'-methyl)phenyl]imino-1-
 isopropylpyrazoline;
3-dimethylaminomethyl-5-imino-4-[(2'-(β-hydroxyethyl)
 amino-4'-hydroxy-5'-methyl)phenyl]imino-1-tert-
 butylpyrazoline;
3-dimethylaminomethyl-5-imino-4-[(2'-(β-hydroxyethyl)
 amino-4'-hydroxy-5'-methyl)phenyl]imino-1-
 phenylpyrazoline;
3-dimethylaminomethyl-5-imino-4-[(2'-(β-hydroxyethyl)
 amino-4'-hydroxy-5'-methyl)phenyl]imino-1-
 benzylpyrazoline;
3-dimethylaminomethyl-5-imino-4-[(2'-(β-hydroxyethyl)
 amino-4'-hydroxy-5'-methyl)phenyl]imino-1-(β-
 hydroxyethyl)pyrazoline;
3-dimethylaminomethyl-5-imino-4-[(2', 4'-diamino-5'-(β-
 hydroxyethyloxy))phenyl]iminopyrazoline;
3-dimethylaminomethyl-5-imino-4-[(2', 4'-diamino-5'-(β-
 hydroxyethyloxy))phenyl]imino-1-methylpyrazoline;
3-dimethylaminomethyl-5-imino-4-[(2', 4'-diamino-5'-(β-
 hydroxyethyloxy))phenyl]imino-1-ethylpyrazoline;
3-dimethylaminomethyl-5-imino-4-[(2', 4'-diamino-5'-(β-
 hydroxyethyloxy))phenyl]imino-1-isopropylpyrazoline;
3-dimethylaminomethyl-5-imino-4-[(2', 4'-diamino-5'-(β-
 hydroxyethyloxy))phenyl]imino-1-tert-butylpyrazoline;
3-dimethylaminomethyl-5-imino-4-[(2', 4'-diamino-5'-(β-
 hydroxyethyloxy))phenyl]imino-1-phenylpyrazoline;
3-dimethylaminomethyl-5-imino-4-[(2', 4'-diamino-5'-(β-
 hydroxyethyloxy))phenyl]imino-1-benzylpyrazoline;
3-dimethylaminomethyl-5-imino-4-[(2', 4'-diamino-5'-(β-
 hydroxyethyloxy))phenyl]imino-1-(β-hydroxyethyl)
 pyrazoline;
as well as their corresponding 4-ylideneamino-5-
aminopyrazole tautomeric form, and mixtures thereof.
 Among the compounds of the invention which are more
particularly preferred, mention may be made of:
5-imino-4-[(2'-amino-4'-hydroxy-5'-methyl)phenyl]imino-
 1,3-dimethylpyrazoline;
5-imino-4-[(2'-amino-4'-hydroxy-5'-methyl)phenyl]
 iminopyrazoline;
5-imino-4-[(2'-amino-4'-hydroxy-5'-methyl)phenyl]imino-
 1-methylpyrazoline;
5-imino-4-[(2'-amino-4'-hydroxy-5'-methyl)phenyl]imino-
 3-methylpyrazoline;
5-imino-4-[(2'-amino-4'-hydroxy)phenyl]imino-1,3-
 dimethylpyrazoline;
5-imino-4-[(2'-amino-4'-hydroxy)phenyl]imino-1-
 methylpyrazoline;
5-imino-4-[(2'-amino-4'-hydroxy)phenyl]iminopyrazoline;
5-imino-4-[(2'-amino-4'-hydroxy)phenyl]imino-3-
 methylpyrazoline;

1-ethyl-5-imino-4-[(2'-amino-4'-hydroxy-5'-methyl)phenyl]
imino-3-methylpyrazoline;
1-ethyl-5-imino-4-[(2'-amino-4'-hydroxy-5'-methyl)phenyl]
iminopyrazoline;
1-ethyl-5-imino-4-[(2'-amino-4'-hydroxy)phenyl]imino-3-methylpyrazoline;
1-ethyl-5-imino-4-[(2'-amino-4'-hydroxy)phenyl]-iminopyrazoline;
1-isopropyl-5-imino-4-[(2'-amino-4'-hydroxy-5'-methyl)phenyl]iminopyrazoline;
1-isopropyl-5-imino-4-[(2'-amino-4'-hydroxy-5'-methyl)phenyl]imino-3-methylpyrazoline;
1-isopropyl-5-imino-4-[(2'-amino-4'-hydroxy)phenyl]iminopyrazoline;
1-isopropyl-5-imino-4-[(2'-amino-4'-hydroxy)phenyl]imino-3-methylpyrazoline;
1-(β-hydroxyethyl)-5-imino-4-[(2'-amino-4'-hydroxy)phenyl]iminopyrazoline;
1-(β-hydroxyethyl)-5-imino-4-[(2'-amino-4'-hydroxy)phenyl]imino-3-methylpyrazoline;
1-(β-hydroxyethyl)-5-imino-4-[(2'-amino-4'-hydroxy-5'-methyl)phenyl]iminopyrazoline;
1-(β-hydroxyethyl)-5-imino-4-[(2'-amino-4'-hydroxy-5'-methyl)phenyl]imino-3-methylpyrazoline;
5-imino-4-[(2'-amino-4'-hydroxy-5'-methyl)phenyl]imino-3-trifluoromethylpyrazoline;
1-methyl-5-imino-4-[(2'-amino-4'-hydroxy-5'-methyl)phenyl]imino-3-trifluoromethylpyrazoline;
5-imino-4-[(2'-amino-4'-hydroxy)phenyl]imino-3-trifluoromethylpyrazoline;
1-ethyl-5-imino-4-[(2'-amino-4'-hydroxy-5'-methyl)phenyl]imino-3-trifluoromethylpyrazoline;
1-ethyl-5-imino-4-[(2'-amino-4'-hydroxy)phenyl]imino-3-trifluoromethylpyrazoline;
1-isopropyl-5-imino-4-[(2'-amino-4'-hydroxy-5'-methyl)phenyl]imino-3-trifluoromethylpyrazoline;
1-isopropyl-5-imino-4-[(2'-amino-4'-hydroxy)phenyl]imino-3-trifluoromethylpyrazoline;
1-(β-hydroxyethyl)-5-imino-4-[(2'-amino-4'-hydroxy)phenyl]imino-3-trifluoromethylpyrazoline;
1-(β-hydroxyethyl)-5-imino-4-[(2'-amino-4'-hydroxy-5'-methyl)phenyl]imino-3-trifluoromethylpyrazoline;
as well as their corresponding 4-ylideneamino-5-aminopyrazole tautomeric form, and mixtures thereof, when tautomeric equilibrium is possible.

Another subject of the invention is the use of the compounds of formula (I) and (II) as direct dyes in, or for the preparation of, dye compositions for keratin fibres.

An additional subject of the invention is a direct dye composition for keratin fibres, in particular for human keratin fibres such as the hair, wherein the composition comprises, in a medium which is suitable for dyeing, at least one direct dye as defined above by formula (I) or (II).

A further subject of the invention is a ready-to-use lightening dye composition for keratin fibres, in particular for human keratin fibres such as the hair, containing in a medium which is suitable for dyeing, at least one direct dye of formula (I) or (II) defined above, with an oxidizing agent, and also a basifying agent in an amount which is sufficient to adjust the final pH to a value above 7, and preferably to a pH value ranging from 8.5 to 11.

However, other characteristics, aspects and advantages of the invention will become more apparent upon reading the description which follows, as well as the various concrete, but in no way limiting, examples intended to illustrate it.

The concentration of a compound of formula (I) or (II) preferably ranges from 0.001 to 5%, and more preferably ranges from 0.01 to 3% by weight, relative to the total weight of the dye composition, before it is applied to the fibres.

The dye composition according to the invention may also contain, in order to obtain varied shades, in addition to the dyes of formula (I) or (II), other direct dye(s) conventionally used, and in particular nitrobenzene dyes, for instance nitrophenylenediamines, nitrodiphenylamines, nitroanilines, nitrophenol ethers or nitrophenols, nitropyridines, anthraquinone, monoazo or diazo, triarylmethane, azine, acridine and xanthene dyes or alternatively metalliferous dyes.

Among the nitrobenzene dyes which can be used in combination with the dyes of formula (I) or (II), mention may preferably be made of:
3-amino-4-hydroxynitrobenzene;
2-amino-3-hydroxynitrobenzene;
2-amino-4-hydroxynitrobenzene;
2-amino-5-hydroxynitrobenzene;
5-amino-2-hydroxynitrobenzene;
2-amino-5-N,N-bis(β-hydroxyethyl)aminonitrobenzene;
2-amino-4-chloro-5-N-(β-hydroxyethyl)aminonitrobenzene;
2-amino-4-methyl-5-N-(β-hydroxyethyl)aminonitrobenzene;
3,4-bis-N-(β-hydroxyethyl)aminonitrobenzene;
2-amino-4-methyl-5-N-(β,γ-dihydroxypropyl)aminonitrobenzene;
2-amino-4-methyl-5-N-(β-aminoethyl)aminonitrobenzene;
1-amino-2-[tris(hydroxymethyl)methyl]amino-5-nitrobenzene;
1-hydroxy-2-N-(β-hydroxyethyl)amino-4,6-dinitrobenzene;
4-N-(β-hydroxyethyl)amino-3-nitrochlorobenzene;
4-N,N-bis(β-hydroxyethyl)amino-1-N-(β-methoxyethyl)amino-2-nitrobenzene;
1-N-(β,γ-dihydroxypropyl)amino-4-N-ethyl-N-(β-hydroxyethyl)amino-2-nitrobenzene;
1-N-(β,γ-dihydroxypropyl)amino-4-N-methyl-N-(β-hydroxyethyl)amino-2-nitrobenzene;
1-N-methylamino-4-N-methyl-N-(β,γ-dihydroxypropyl)amino-2-nitrobenzene;
2-chloro-6-ethylamino-1-hydroxynitrobenzene;
2-N,N-bis(β-hydroxyethyl)amino-1-hydroxy-5-nitrobenzene;
1-N-(β-hydroxyethyl)amino-2-nitro-4-trifluoromethylbenzene;
4-ethylamino-3-nitrobenzoic acid;
4-amino-2-nitrodiphenylamine-2-carboxylic acid;
4-amino-4'-dimethylamino-2-nitrodiphenylamine-2'-carboxylic acid;
and more preferably of:
3,4-diaminonitrobenzene;
2,5-diaminonitrobenzene;
2-amino-1-hydroxy-4,6-dinitrobenzene;
2-amino-5-N-(β-hydroxyethyl)aminonitrobenzene;
2-N-(β-hydroxyethyl)amino-5-N,N-bis(β-hydroxyethyl)aminonitrobenzene;
2-N-methylamino-5-N,N-bis(β-hydroxyethyl)aminonitrobenzene;
2-N-methylamino-5-N-methyl-N-(β-hydroxyethyl)aminonitrobenzene;
2-N-(β-hydroxyethyl)amino-5-hydroxynitrobenzene;
4-N-(β-hydroxyethyl)amino-3-methoxynitrobenzene;
2-N-(β-hydroxyethyl)amino-5-aminonitrobenzene;
2-N-(β-hydroxyethyl)aminonitrobenzene;

3-amino-4-N-(β-hydroxyethyl)aminonitrobenzene;
3-β-hydroxyethyloxy-4-(N-(β-hydroxyethyl) aminonitrobenzene;
2-amino-5-N-methylaminonitrobenzene;
2-amino-3-methylnitrobenzene;
2-N-(β-hydroxyethyl)amino-5-β,γ-dihydroxypropyloxynitrobenzene;
3-hydroxy-4-N-(β-hydroxyethyl)aminonitrobenzene;
4-amino-3-hydroxynitrobenzene;
2,5-N,N'-(β-hydroxyethyl)aminonitrobenzene;
2-N-methylamino-4-β,γ-dihydroxypropyloxynitrobenzene;
2-N-(β-aminoethyl)amino-5-N,N-bis(β-hydroxyethyl) aminonitrobenzene;
2-N-(β-aminoethyl)amino-4-methoxynitrobenzene;
2-N-(γ-aminoethyl)amino-5-β-hydroxyethyloxynitrobenzene;
4'-hydroxy-2-nitrodiphenylamine;
4-amino-2-nitrodiphenylamine;
1-N-(β-ureidoethyl)amino-4-nitrobenzene;
4-N-ethyl-N-(β-hydroxyethyl)amino-1-(β-hydroxyethyl) amino-2-nitrobenzene;
4-N-(β,γ-dihydroxypropyl)amino-3-nitrotrifluoromethylbenzene;
4-N-(β-hydroxyethyl)amino-3-nitromethylbenzene;
1-N-(β-hydroxyethyl)amino-4-N,N-bis(β-hydroxyethyl) amino-2-nitrobenzene;
2-amino-6-chloro-4-nitrophenol;
4-chloro-1,3-diamino-6-nitrobenzene; and
1-hydroxy-4-N-(γ-hydroxypropyl)amino-3-nitrobenzene.

Among the anthraquinone dyes which can be used in combination with the dyes of formula (I) or (II), it is preferred to use the dyes known under the names DISPERSE VIOLET 4, DISPERSE BLUE 1, ACID VIOLET 43, DISPERSE VIOLET 1, DISPERSE RED 11, ACID BLUE 62, C.I. MORDANT RED 3, in the Color Index, 3rd Edition, as well as (4-hydroxyanthraquinonyl-1-aminopropyl)methylmorpholinium methyl sulphate.

Among the nitropyridines which can be used in combination with the dyes of formula (I) or (II), it is preferred to use:
2,5-diamino-6-nitropyridine;
5-amino-2-N-(β-hydroxyethyl)amino-6-nitropyridine;
2-amino-5-N-(β-hydroxyethyl)amino-6-nitropyridine;
5-amino-2-N-ethylamino-6-nitropyridine;
2-N-ethylamino-5-N-(β-hydroxyethyl)amino-6-nitropyridine; and
2-N-methylamino-5-N-(β-hydroxyethyl)amino-6-nitropyridine.

Among the azo dyes which can be used in combination with the dyes of formula (I) or (II), it is preferred to use those known under the names DISPERSE YELLOW 3, BASIC RED 76, BASIC BROWN 16, BASIC YELLOW 57, ACID YELLOW 36, FOOD RED 1, ACID ORANGE 7, ACID RED 88, FOOD YELLOW 3, ACID RED 184, ACID ORANGE 24, BASIC BROWN 4, ACID RED 35, DISPERSE RED 17, DISPERSE BLACK 5, in the Color Index.

Among the triarylmethane dyes which can be used in combination with the dyes of formula (I) or (II), it is preferred to use those known under the names BASIC GREEN 1, BASIC VIOLET 14, BASIC VIOLET 1, BASIC VIOLET 3, BASIC BLUE 26, in the Color Index.

Among the other families of direct dyes which are mentioned above and which can be used more preferably in combination with the dyes of formula (I) or (II), in particular among the azine dyes, mention may preferably be made of: BASIC RED 2, among the acridine dyes, mention may be made preferably of acridine orange, referred to as BASIC ORGANGE 14 in the Color Index, and among the xanthene dyes, mention may preferably be made of rhodamine B, referred to as BASIC VIOLET 10 in the Color Index.

The proportion of all these other additional direct dyes preferably ranges approximately from 0.05 to 10% by weight relative to the total weight of the dye composition.

The dyes of formula (I) or (II) may also be incorporated into dye compositions for oxidation dyeing which contain oxidation bases and optionally couplers, in order to enrich with glints the shades obtained with the oxidation dyes.

The appropriate medium for dyeing is preferably an aqueous medium comprising water, and optionally a cosmetically acceptable organic solvent, and more preferably alcohols, such as ethyl alcohol, isopropyl alcohol, benzyl alcohol or phenylethyl alcohol, or glycols or glycol ethers such as, for example, ethylene glycol and the monomethyl, monoethyl and monobutyl ethers thereof, propylene glycol or ethers thereof such as, for example, propylene glycol monomethyl ether, butylene glycol and dipropylene glycol, as well as diethylene glycol alkyl ethers such as, for example, diethylene glycol monoethyl ether or monobutyl ether. The organic solvent is preferably present in amounts ranging approximately from 0.5 to 20%, and more preferably approximately from 2 to 10% by weight, relative to the total weight of the composition.

Fatty amides such as mono- and diethanolamides of acids derived from coconut, from lauric acid, or from oleic acid may also be added to the composition according to the invention, preferably in an amount ranging approximately from 0.05 to 10% by weight.

Surfactants which are well known in the art, such as, anionic, cationic, nonionic, amphoteric or zwitterionic surfactants or mixtures thereof may also be added to the composition according to the invention, preferably in an amount ranging approximately from 0.1 to 50% by weight, and more preferably approximately from 1 to 20% by weight, relative to the total weight of the composition.

Thickeners may also be used in amounts preferably ranging approximately from 0.2 to 5%.

The dye composition may also contain various common adjuvants such as antioxidants, fragrances, sequestering agents, dispersing agents, hair conditioners, preserving agents and opacifiers, as well as any other adjuvant usually used in cosmetics.

The dye composition according to the invention may be formulated at acidic, neutral or alkaline pH, it being possible for the pH to range, for example, from 4 to 11 and preferably from 5 to 10, and it being possible for the pH to be adjusted using basifying agents or acidifying agents that are well known in the art.

Among the basifying agents which may preferably be mentioned are aqueous ammonia, alkaline carbonates, alkanolamines, for example, mono-, di- and triethanolamines and derivatives thereof, sodium hydroxide, potassium hydroxide and the compounds of formula:

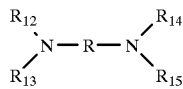

wherein R is a propylene residue optionally substituted with a hydroxyl group or a $C_1$–$C_4$ alkyl radical; $R_{12}$, $R_{13}$, $R_{14}$ and $R_{15}$, which may be identical or different, represent a hydrogen atom, a $C_1$–$C_4$ alkyl radical or a $C_1$–$C_4$ hydroxyalkyl radical.

The acidifying agents are preferably inorganic or organic acids such as, for example, hydrochloric acid, tartaric acid, citric acid and phosphoric acid.

When the dye composition according to the invention constitutes a lightening dye, the pH of composition (A) which contains at least one direct dye of formula (I) or (II), as well as that of composition (B) containing the oxidizing agent, are such that, after composition (A) is mixed with composition (B), the pH of the composition (mixture) applied to the human keratin fibres is above 7, and preferably ranges from 8.5 to 11. It is adjusted to the selected value using basifying and optionally acidifying agents that are well known and described above, for example.

The oxidizing agent is preferably selected from hydrogen peroxide, urea peroxide, alkali metal bromates and persalts, such as perborates and persulphates. It is particularly preferred to use hydrogen peroxide.

The oxidizing composition (B) preferably comprises an aqueous hydrogen peroxide solution whose titre preferably ranges approximately from 5 to 40 volumes. The basifying agent is preferably selected from alkanolamines when moderate lightening is required, and it is more preferably aqueous ammonia when more considerable lightening is desired.

The composition applied to the hair may be in various forms, such as in liquid, cream, or gel form, or in any other form which is suitable for dyeing keratin fibres. Preferably, the composition may be packaged under pressure in an aerosol can in the presence of a propellant and may form a foam.

Another subject of the present invention relates to a process for dyeing keratin fibres, in particular human keratin fibres such as the hair, by direct dyeing, this process comprises leaving a dye composition containing at least one direct dye of formula (I) or (II) to act on the dry or wet keratin fibres. The composition according to the invention may be used as a leave-in composition, i.e., after applying the composition to the fibres, the fibres are dried without intermediate rinsing. In other modes of application, the composition is left to act on the fibres for an exposure time ranging approximately from 3 to 60 minutes, preferably approximately from 5 to 45 minutes, after which the fibres are rinsed, optionally washed and then rinsed again and dried.

A still further subject of the invention is a process for dyeing keratin fibres, in particular human keratin fibres such as the hair, this process comprising applying to these fibres at least one composition (A) containing, in a medium which is suitable for dyeing, at least one direct dye of formula (I) or (II), the lightening being ensured, at a pH above 7, using an oxidizing agent which is mixed with composition (A) only at the time of use, or which is present in a composition (B) that is applied simultaneously.

An additional subject of the invention is multi-compartment dyeing "kits" or devices, a first compartment of which contains at least one direct dye of formula (I) or (II), as well as a basifying agent, and a second compartment of which contains an oxidizing agent. Another alternative "kit" is composed of a first compartment comprising at least one dye of formula (I) or (II), a second compartment comprising a basifying agent and a third compartment comprising an oxidizing agent.

Still another subject of the present invention relates to novel 4,5-diiminopyrazolines of formula (I'):

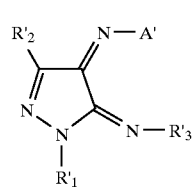

and 4-ylideneamino-5-aminopyrazole tautomeric forms thereof formula (II'):

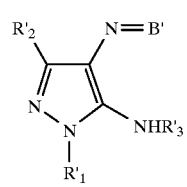

wherein
$R'_1$, $R'_2$, $R'_3$, A' and B' are defined identically to the radicals $R_1$, $R_2$, $R_3$, A and B of formulae (I) and (II) defined above, with the proviso that
(i) when $R'_1$ represents phenyl, $R'_2$ represents methyl and $R'_3$ represents hydrogen, A' is other than 4-dimethylaminophenyl and 4-diethylaminophenyl; and
(ii) when $R'_1$, $R'_2$ and $R'_3$ represent hydrogen, A' is other than the para-(2-methyl-5-aminophenol) and para-(1,3-diaminobenzene) radicals.

The compounds of formula (I') may be obtained according to a conventionally known preparation process, according to which a 5-aminopyrazole (1) is reacted with a benzene compound (2) in the presence of an oxidizing agent such as potassium ferricyanide, and preferably in a proportion of 1 to 3 molar equivalents, in order to obtain a 4,5-diiminopyrazoline of formula (I'), as indicated in the following scheme:

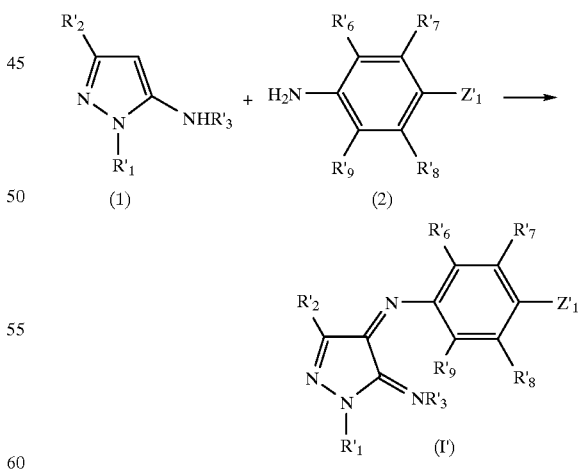

The reaction is preferably carried out at a temperature ranging from 5 to 50° C. in a water/pyridine mixture buffered to pH 8 using a phosphate or carbonate buffer, the pyridine content preferably being less than 30%.

The compounds of formula (II') may be obtained according to a preparation process, which itself constitutes another subject of the present invention, this process comprises reacting a 4,5-diaminopyrazole (3) with a benzene compound (4) so as to obtain a 4,5-diaminopyrazole of formula (II'), according to the following scheme:

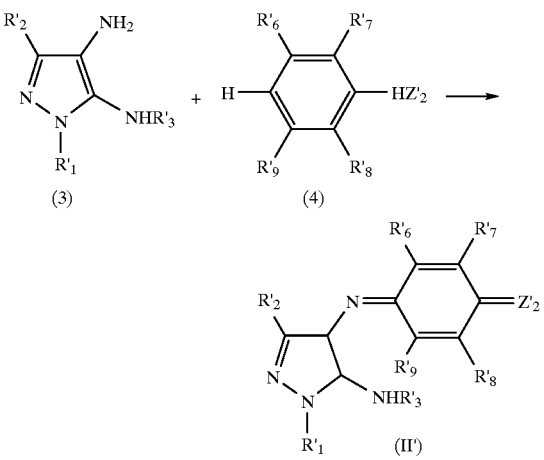

The reaction is carried out at a temperature preferably ranging from 10° C. to 60° C., in aqueous-alcoholic medium, the alcohol preferably being selected from lower alcohols such as methanol, ethanol and isopropanol.

The compounds (3) and (4) may be in the form of free bases or organic or inorganic salts. When they are in the form of free bases, the pH of the reaction is a spontaneous pH. When one of the compounds (3) or (4), or both compounds (3) and (4), are in the form of salts, a base is used in stoichiometric amount, and is preferably sodium, potassium or lithium hydroxide.

The compound (4) is preferably a compound of formula:

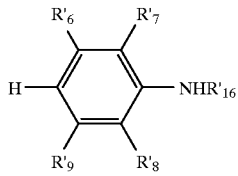

wherein $R'_6$, $R'_7$, $R'_8$ and $R'_9$ have the same meanings as the radicals $R_6$ to $R_9$ defined above and $R'_{16}$ represents hydrogen or a linear or branched $C_1$–$C_4$ alkyl, or a compound of formula:

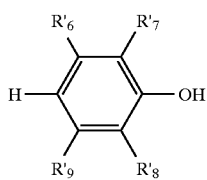

wherein $R'_6$, $R'_7$, $R'_8$ and $R'_9$ have the same meanings as above.

Concrete examples illustrating the invention will now be given.

PREPARATION EXAMPLES
Example 1
Preparation of 5-amino-2-methyl-N-(5-aminopyrazol-4-yl)-p-quinone monoimine (II'a)

31 g (0.25 mol) of 5-amino-2-methylphenol dissolved in 400 cm³ of ethanol 5 was added, at room temperature, to a solution of 43 g (0.25 mol) of 4,5-diaminopyrazole dihydrochloride in 500 cm³ of water. 32 g (0.5 mol) of potassium hydroxide dissolved in 80 cm³ of water was then added, at 25° C. After bubbling air through for 48 h with stirring, the reaction medium was cooled to 0° C. and the precipitate was filtered off, washed with 100 cm³ of water and dried under 30 mmHg at 40° C.

27 g of 5-amino-2-methyl-N-(5-aminopyrazol-4-yl)-p-quinone monoimine (II'a) were obtained in the form of a brown-red solid; the melting point of which ranged from 250° C. to 251° C.

The elemental analysis for $C_{10}H_{11}N_5O.1H_2O$ was:

| % | C | H | N | O |
|---|---|---|---|---|
| theory | 51.05 | 5.57 | 29.77 | 13.60 |
| found | 51.10 | 5.60 | 29.75 | 13.75 |

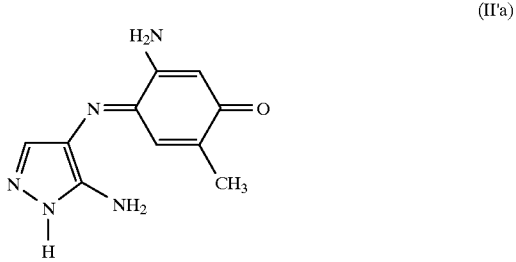

(II'a)

During its use in the dye compositions, this compound may convert into its corresponding 5-imino-4-[(2'-amino-4'-hydroxy-5'-methyl)phenyl]iminopyrazoline tautomeric form according to a tautomeric equilibrium.

Example 2

Preparation of 5-amino-2-methyl-N-(5-amino-1-methylpyrazol-4-yl)-p-quinone monoimine (II'b).

31 g (0.25 mol) of 5-amino-2-methylphenol dissolved in 400 cm³ of ethanol was added, at room temperature, to a solution of 46 g (0.25 mol) of 4,5-diamino-1-methylpyrazole dihydrochloride in 500 cm³ of water. 32 g (0.5 mol) of potassium hydroxide dissolved in 80 cm³ of water was then added, at 25° C. After bubbling air through for 48 h with stirring, the reaction medium was cooled to 0° C. and the precipitate was filtered off, washed with 100 cm³ of water, and dried under vacuum at 40° C.

56g of 5-amino-2-methyl-N-(5-amino-1-methylpyrazol-4-yl)-p-quinone monoimine (II'b) were obtained in the form of a red-brown solid; the melting point of which was 160° C.

The elemental analysis for $C_{11}H_{13}N_5O \cdot 1H_2O$ was:

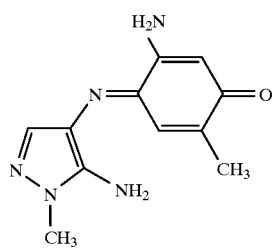

(II'b)

During its use in dye compositions, this compound may convert into its corresponding 5-imino-4-[(2'-amino-4'-hydroxy-5'-methyl)phenyl]imino-1-methylpyrazoline tautomeric form, according to a tautomeric equilibrium.

Example 3

Preparation of 5-amino-2-methyl-N-(5-amino-1,3-dimethylpyrazol-4-yl)-p-quinone monoimine (II'c).

31 g (0.25 mol) of 5-amino-2-methylphenol dissolved in 400 cm³ of ethanol was added, at room temperature, to a solution of 50 g (0.25 mol) of 4,5-diamino-1,3-dimethylpyrazole dihydrochloride in 500 cm³ of water. 32 g (0.5 mol) of potassium hydroxide dissolved in 80 cm³ of water was then added, at 25° C. After bubbling air through for 48 h with stirring, the reaction medium was cooled to 0° C. and the precipitate was filtered off, washed with 100 cm³ of water, and dried under vacuum at 40° C.

30 g of 5-amino-2-methyl-N-(5-amino-1,3-dimethylpyrazol-4-yl)-p-quinone monoimine (II'c) were obtained in the form of a brown solid; the melting point of which was between 245° C. and 246° C.

The elemental analysis for $C_{12}H_{15}N_5O \cdot 1H_2O$ was:

| %     | C     | H    | N     | O     |
|-------|-------|------|-------|-------|
| theory | 54.70 | 6.51 | 26.60 | 12.15 |
| found  | 54.45 | 6.52 | 26.60 | 12.00 |

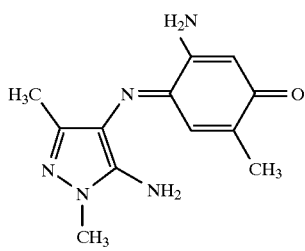

(II'c)

During its use in dye compositions, this compound may convert into its corresponding 5-imino-4-[(2'-amino-4'-hydroxy-5'-methyl)phenyl]imino-1,3-dimethylpyrazoline tautomeric form, according to a tautomeric equilibrium.

EXAMPLE OF DYE COMPOSITIONS

Example 4

The following dye composition was prepared:
Oleyl alcohol polyglycerolated with 2 mol of glycerol . . . 4.0 g
Oleyl alcohol polyglycerolated with 4 mol of glycerol (containing 78% AM) . . . 5.69 g AM*
Oleic acid . . . 3.0 g
Oleylamine oxyethylenated with 2 mol of ethylene oxide . . . 7.0 g
Diethylaminopropyl laurylamino-succinamate, sodium salt (containing 55% AM) . . . 3.0 g AM
Oleyl alcohol . . . 5.0 g
Oleic acid diethanolamide . . . 12.0 g
Propylene glycol . . . 3.5 g
Ethyl alcohol . . . 7.0 g
Dipropylene glycol . . . 0.5 g
Propylene glycol monomethyl ether . . . 9.0 g
Fragrance, preserving agent . . . q.s.
Monoethanolamine q.s. . . . pH 9.8
2-Amino-5-N-(β-hydroxyethyl)-aminonitrobenzene . . . 0.15 g
Compound prepared in Example 3 . . . 0.5 g
Demineralized water q.s. . . . 100 g
Active material The above composition was mixed with twice its weight of 9-volumes aqueous hydrogen peroxide solution.

The mixture obtained was applied to locks of natural grey hair containing 90% white hairs and was allowed to remain on the hair for 15 minutes. After rinsing with running water, washing with a standard shampoo and drying, the locks were dyed in an iridescent ash shade.

Example 5

The following dye composition was prepared:
2-N-Methylamino-4-β,γ-dihydroxypropyloxynitrobenzene . . . 0.2 g
Compound prepared in Example 2 . . . 0.4 g
Propylene glycol monomethyl ether . . . 10 g
Sodium lauryl ether sulphate oxyethylenated with 2.2 mol of ethylene oxide (containing 28% AM) . . . 5.6 g AM*
2-Amino-2-methyl-1-propanol q.s. . . . pH 7
Demineralized water q.s. . . . 100 g
Active material The above composition was applied to locks of natural or permanent-waved grey hair containing 90% white hairs and was allowed to remain on the hair for 30 minutes. After rinsing with running water and drying, the locks were dyed in a golden coppery shade.

Example 6

The following dye composition was prepared:
Compound prepared in Example 3 . . . 0.5 g
Ethanol . . . 10.0 g
Monoethanolamine q.s. . . . pH 10
Water q.s. . . . 100 g The above composition was applied to locks of permanent-waved grey hair containing 90% white hairs and was allowed to remain on the hair for 30 minutes. After rinsing with running water, washing with a standard shampoo, rinsing again and drying, the hair was dyed in a violet-pink shade.

Example 7

The following dye composition was prepared:
Compound prepared in Example 3 . . . 1.0 g
Ethanol . . . 10 g
Aqueous 20% $NH_3$ solution q.s. . . . pH 10.5
Water q.s. . . . 100 g The above composition was mixed with its weight of 20-volumes aqueous hydrogen peroxide solution.

The mixture obtained was applied to locks of permanent-waved grey hair containing 90% white hairs and was allowed to remain on the hair for 30 minutes. After rinsing with running water, washing with a standard shampoo, rinsing and drying, the hair was dyed in a fuchsia-pink shade.

What is claimed is:

1. A dye composition for keratin fibres, comprising, in a medium suitable for dyeing, at least one dye, said at least one dye being a 4,5-diiminopyrazoline compound of formula (I):

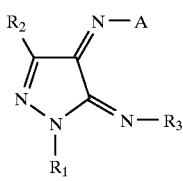
(I)

or a 4-ylideneamino-5-aminopyrazole tautomeric form thereof of formula (II):

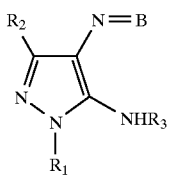
(II)

wherein:

$R_1$ and $R_3$, which may be identical or different, represent a hydrogen atom; a $C_1$–$C_6$ alkyl radical; a $C_2$–$C_4$ hydroxyalkyl radical; a $C_2$–$C_4$ aminoalkyl radical; a phenyl radical; a phenyl radical substituted with a halogen atom or with a $C_1$–$C_4$, alkyl, $C_1$–$C_4$ alkoxy, nitro, trifluoromethyl, amino or $C_1$–$C_4$ alkylamino radical; a benzyl radical; a benzyl radical substituted with a halogen atom or with a $C_1$–$C_4$ alkyl, $C_1$–$C_4$ alkoxy, methylenedioxy or amino radical; or a radical:

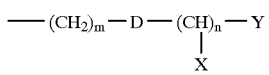

wherein m and n, which may be identical or different, represent an integer ranging from 1 to 3;

D represents oxygen or —NH—;

X represents hydrogen or $CH_3$;

Y represents $CH_3$ or $OR_4$, wherein $R_4$ represents hydrogen, methyl or ethyl;

and $R_3$ may also represent an amino radical;

$R_2$ represents a hydrogen atom; a $C_1$–$C_6$ alkyl radical; a $C_1$–$C_4$ hydroxyalkyl radical; a $C_1$–$C_4$ aminoalkyl radical; a $C_1$–$C_2$ alkylthio radical; a $C_1$–$C_5$ alkoxy radical; a trifluoromethyl, cyano or carboxyl radical; a phenyl radical; a phenyl radical substituted with a halogen atom or with a $C_1$–$C_4$ alkyl, $C_1$–$C_4$ alkoxy, nitro, trifluoromethyl, amino or $C_1$–$C_4$ alkylamino radical; a benzyl radical; a benzyl radical substituted with a halogen atom or with a $C_1$–$C_4$ alkyl, $C_1$–$C_4$ alkoxy, nitro, trifluoromethyl, amino or $C_1$–$C_4$ alkylamino radical; a heterocycle selected from thiophene, furan or pyridine; or a radical:

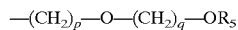

wherein p and q, which may be identical or different, represent integers ranging from 1 to 3; and $R_5$ represents hydrogen or methyl;

A represents a radical:

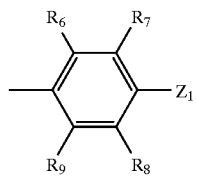

and

B represents a radical:

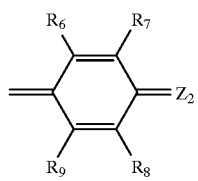

wherein, $Z_1$ represents a hydroxyl radical; a $C_1$–$C_4$ alkoxy radical; an amino radical; an acetamido radical; a $C_1$–$C_4$ alkylamino radical; a $C_1$–$C_4$ hydroxyalkylamino radical; a $C_1$–$C_4$ aminoalkylamino radical; or a radical $NR_{10}R_{11}$, wherein $R_{10}$ and $R_{11}$, which may be identical or different, represent a $C_1$–$C_4$ alkyl, $C_2$–$C_4$ hydroxyalkyl or $C_2$–$C_4$ aminoalkyl radical;

$R_6$, $R_7$, $R_8$ and $R_9$, which may be identical or different, represent a hydrogen atom; a $C_1$–$C_4$ alkyl radical; a $C_1$–$C_4$ alkoxy radical; a $C_1$–$C_4$ alkylthio radical; an amino radical; a $C_1$–$C_4$ alkylamino radical; a carbamoylmethylamino radical; a $C_2$–$C_4$ hydroxyalkyl radical; a $C_2$–$C_4$ monohydroxyalkoxy radical; a $C_2$–$C_4$ dihydroxyalkoxy radical; a $C_1$–$C_2$ carboxyalkoxy radical; a chlorine, bromine or fluorine atom; a $C_1$–$C_2$ trifluoroalkyl radical;

a radical:

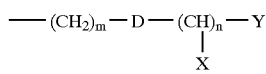

wherein m and n have the same meanings as recited above, and D, X and Y have the same meanings as recited above; or a radical $NR_{10}R_{11}$, wherein $R_{10}$ and $R_{11}$ have the same meanings as recited above; and $Z_2$ represents O or NR, wherein R represents hydrogen or an acetyl, $C_1$–$C_4$ alkyl, $C_1$–$C_4$ hydroxyalkyl or $C_1$–$C_4$ aminoalkyl radical;

it being understood that each of the alkyl or alkoxy radicals of the groups defined above may be linear or branched with the proviso that:

(i) when $R_1$ represents phenyl, $R_2$ represents methyl and $R_3$ represents hydrogen, A is other than 4-dimethylaminophenyl and 4-diethylaminophenyl; and (ii) when $R_1$, $R_2$ and $R_3$ represent hydrogen, A is other than para-(2-methyl-5-aminophenol) and para-(1,3-diaminobenzene) radicals.

2. A composition according to claim 1, wherein said at least one dye is a:

5-imino-4-[(2'-amino-4'-hydroxy-5'-methyl)phenyl]imino-1,3-dimethylpyrazoline;

5-imino-4-[(2'-amino-4'-hydroxy-5'-methyl)phenyl]imino-1-methylpyrazoline;

5-imino-4-[(2'-amino-4'-hydroxy-5'-methyl)phenyl]imino-3-methylpyrazoline;

5-imino-4-[(2'-amino-4'-hydroxy)phenyl]imino-1,3-dimethylpyrazoline;

5-imino-4-[(2'-amino-4'-hydroxy)phenyl]imino-1-methylpyrazoline;

5-imino-4-[(2'-amino-4'-hydroxy)phenyl]iminopyrazoline;

5-imino-4-[(2'-amino-4'-hydroxy)phenyl]imino-3-methylpyrazoline;

1-ethyl-5-imino-4-[(2'-amino-4'-hydroxy-5'-methyl)phenyl]imino-3-methylpyrazoline;

1-ethyl-5-imino-4-[(2'-amino-4'-hydroxy-5'-methyl)phenyl]iminopyrazoline;

1-ethyl-5-imino-4-[(2'-amino-4'-hydroxy)phenyl]imino-3-methylpyrazoline;

1-ethyl-5-imino-4-[(2'-amino-4'-hydroxy)phenyl]iminopyrazoline;

1-isopropyl-5-imino-4-[(2'-amino-4'-hydroxy-5'-methyl)phenyl]iminopyrazoline;

1-isopropyl-5-imino-4-[(2'-amino-4'-hydroxy-5'-methyl)phenyl]imino-3-methylpyrazoline;

1-isopropyl-5-imino-4-[(2'-amino-4'-hydroxy)phenyl]iminopyrazoline;

1-isopropyl-5-imino-4-[(2'-amino-4'-hydroxy)phenyl]imino-3-methylpyrazoline;

1-(β-hydroxyethyl)-5-imino-4-[(2'-amino-4'-hydroxy)phenyl]iminopyrazoline;

1-(β-hydroxyethyl)-5-imino-4-[(2'-amino-4'-hydroxy)phenyl]imino-3-methylpyrazoline;

1-(β-hydroxyethyl)-5-imino-4-[(2'-amino-4'-hydroxy-5'-methyl)phenyl]iminopyrazoline;

1-(β-hydroxyethyl)-5-imino-4-[(2'-amino-4'-hydroxy-5'-methyl)phenyl]imino-3-methylpyrazoline 5-imino-4-[(2'-amino-4'-hydroxy-5'-methyl)phenyl]imino-3-trifluoromethylpyrazoline;

1-methyl-5-imino-4-[(2'-amino-4'-hydroxy-5'-methyl)phenyl]imino-3-trifluoromethylpyrazoline;

1-methyl-5-imino-4-[(2'-amino-4'-hydroxy)phenyl]imino-3-trifluoromethylpyrazoline;

5-imino-4-[(2'-amino-4'-hydroxy)phenyl]imino-3-trifluoromethylpyrazoline;

1-ethyl-5-imino-4-[(2'-amino-4'-hydroxy-5'-methyl)phenyl]imino-3-trifluoromethylpyrazoline;

1-ethyl-5-imino-4-[(2'-amino-4'-hydroxy)phenyl]imino-3-trifluoromethylpyrazoline;

1-isopropyl-5-imino-4-[(2'-amino-4'-hydroxy-5'-methyl)phenyl]imino-3-trifluoromethylpyrazoline;

1-isopropyl-5-imino-4-[(2'-amino-4'-hydroxy)phenyl]imino-3-trifluoromethylpyrazoline;

1-(β-hydroxyethyl)-5-imino-4-[(2'-amino-4'-hydroxy)phenyl]imino-3-trifluoromethylpyrazoline;

1-(β-hydroxyethyl)-5-imino-4-[(2'-amino-4'-hydroxy-5'-methyl)phenyl]imino-3-trifluoromethylpyrazoline; or when possible, the corresponding 4-ylideneamino-5-aminopyrazole tautomeric form thereof.

3. A composition according to claim 1, wherein said composition has a pH ranging from 4 to 11.

4. A direct dye composition for keratin fibres, said composition comprising an effective amount of a dye composition according to claim 1.

5. A lightening composition for keratin fibres, said composition comprising an effective amount of a dye composition according to claim 1.

6. A lightening composition according to claim 5, further comprising an oxidizing agent and a basifying agent, each of said agents being present in an amount effective to adjust the final pH of said composition to a value above 7.

7. A composition according to claim 1 wherein said at least one dye is present in an amount ranging from 0.001 to 5% by weight relative to the total weight of the composition.

8. A composition according to claim 7, wherein said at least one dye is present in an amount ranging from 0.01 to 3% by weight relative to the total weight of the composition.

9. A composition according to claim 6, wherein said oxidizing agent is an aqueous hydrogen peroxide solution.

10. A composition according to claim 6, wherein said basifying agent is aqueous ammonia or an alkanolamine.

11. A composition according to claim 6, wherein said basifying agent is present in an amount effective to adjust the final pH of said composition to a value ranging from 8.5 to 11.

12. A composition according to claim 1, further comprising a nitropyridine, nitrobenzene, anthraquinone, monoazo, diazo, triarylmethane, azine, acridine, xanthene or metalliferous dye.

13. A composition according to claim 12, wherein said nitrobenzene dye is a nitrophenylenediamine, nitrodiphenylamine, nitroaniline, nitrophenyl ether, or nitrophenol.

14. A composition according to claim 1, wherein said medium suitable for dyeing is an aqueous medium comprising water or a mixture of water and an organic solvent.

15. A composition according to claim 14, wherein said organic solvent is an alcohol, glycol or glycol ether.

16. A composition according to claim 1, wherein said medium suitable for dyeing does not contain any organic solvent.

17. A composition according to claim 14, wherein said organic solvent is present in an amount ranging from 0.5 to 20% by weight relative to the total weight of the composition.

18. A process for direct dyeing dry keratin fibres, said process comprising the steps of applying to said dry keratin fibres an effective amount of a dyeing composition according to claim 1, and drying said keratin fibres without intermediate rinsing.

19. A process according to claim 18, wherein said dry keratin fibres are human keratin fibres.

20. A process for direct dyeing wet keratin fibres, said process comprising the steps of applying to said wet keratin fibres an effective amount of a dyeing composition according to claim 1, and drying said keratin fibres without intermediate rinsing.

21. A process according to claim 20, wherein said wet keratin fibres are human keratin fibres.

22. A process for direct dyeing dry keratin fibres, said process comprising the steps: (1) applying to said dry keratin fibres an effective amount of a composition according to claim 1; (2) allowing said composition to remain on said keratin fibres for approximately 3 to 60 minutes; (3) rinsing said fibres; (4) optionally washing and rinsing said fibres; and (5) drying said fibres.

23. A process according to claim 22, wherein said dry keratin fibres are human keratin fibres.

24. A process for direct dyeing wet keratin fibres, said process comprising the steps of: (1) applying to said wet keratin fibres an effective amount of a composition according to claim 1; (2) allowing said composition to remain on said keratin fibres for approximately 3 to 60 minutes; (3) rinsing said fibres; (4) optionally washing and rinsing said fibres; and (5) drying said fibres.

25. A process according to claim 24, wherein said wet keratin fibres are human keratin fibres.

26. A process for lightening keratin fibres, said process comprising applying to said keratin fibres an effective amount of a lightening composition according to claim 6.

27. A process according to claim 26, wherein said keratin fibres are human keratin fibres.

28. A process for lightening keratin fibres, said process comprising the steps of: (1) applying to said keratin fibres, at a pH of above 7, an effective amount of a composition according to claim 1; and (2) simultaneously applying to said keratin fibres an effective amount of a separate composition comprising an oxidizing agent.

29. A process according to claim 28, wherein said keratin fibres are human keratin fibres.

30. A multi-compartment kit for lightening human keratin fibres, said kit comprising at least two compartments, wherein a first compartment comprises a composition according to claim 1, and wherein a second compartment comprises a composition comprising an oxidizing agent in a medium suitable for dyeing.

31. A 4,5-diiminopyrazoline dye of formula (I'):

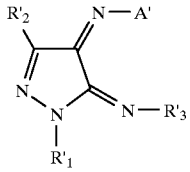

(I')

or the 4-ylideneamino-5-aminopyrazole tautomeric form thereof of formula (II'):

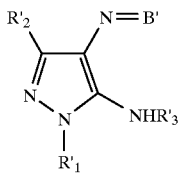

(II')

wherein:

$R'_1$ and $R'_3$, which may be identical or different, represent a hydrogen atom; a $C_1-C_6$ alkyl radical; a $C_2-C_4$ hydroxyalkyl radical; a $C_2-C_4$ aminoalkyl radical; a phenyl radical; a phenyl radical substituted with a halogen atom or with a $C_1-C_4$ alkyl, $C_1-C_4$ alkoxy, nitro, trifluoromethyl, amino or $C_1-C_4$ alkylamino radical; a benzyl radical; a benzyl radical substituted with a halogen atom or with a $C_1-C_4$ alkyl, $C_1-C_4$ alkoxy, methylenedioxy or amino radical; or a radical:

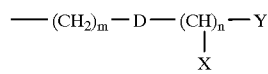

wherein m and n, which may be identical or different, represent an integer ranging from 1 to 3;
D represents oxygen or —NH—;
X represents hydrogen or $CH_3$;
Y represents $CH_3$ or $OR_4$, wherein $R_4$ represents a hydrogen, methyl or ethyl;
and $R'_3$ may also represent an amino radical;

$R'_2$ represents a hydrogen atom; a $C_1-C_6$ alkyl radical; a $C_1-C_4$ hydroxyalkyl radical; a $C_1-C_4$ aminoalkyl radical; a $C_1-C_2$ alkylthio radical; a $C_1-C_5$ alkoxy radical; a trifluoromethyl, cyano or carboxyl radical; a phenyl radical; a phenyl radical substituted with a halogen atom or with a $C_1-C_4$ alkyl, $C_1-C_4$ alkoxy, nitro, trifluoromethyl, amino or $C_1-C_4$ alkylamino radical; a benzyl radical; a benzyl radical substituted with a halogen atom or with a $C_1-C_4$ alkyl, $C_1-C_4$ alkoxy, nitro, trifluoromethyl, amino or $C_1-C_4$ alkylamino radical; a heterocycle selected from thiophene, furan or pyridine; or a radical:

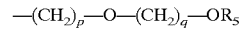

wherein p and q, which may be identical or different, are integers ranging from 1 to 3; and $R_5$ represents hydrogen or methyl;

A' represents a radical:

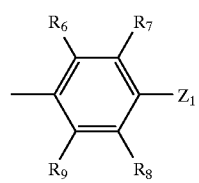

and
B' represents, a radical:

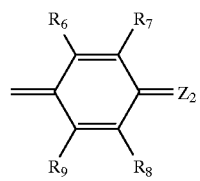

wherein:

$Z_1$ represents a hydroxyl radical; a $C_1-C_4$ alkoxy radical; an amino radical; an acetamido radical; a $C_1-C_4$ alkylamino radical; a $C_1-C_4$ hydroxyalkylamino radical; a $C_1-C_4$ aminoalkylamino radical; a radical $NR_{10}R_{11}$, wherein $R_{10}$ and $R_{11}$, which may be identical or different, represent a $C_1-C_4$ alkyl, $C_2-C_4$ hydroxyalkyl or $C_2-C_4$ aminoalkyl radical;

$R_6$, $R_7$, $R_8$ and $R_9$, which may be identical or different, represent a hydrogen atom; a $C_1-C_4$ alkyl radical; a $C_1-C_4$ alkoxy radical; a $C_1-C_4$ alkylthio radical; an amino radical; a $C_1-C_4$ alkylamino radical; a carbamoylmethylamino radical; a $C_2$–$C_4$ hydroxyalkyl radical; a $C_2$–$C_4$ monohydroxyalkoxy radical; a $C_2$–$C_4$ dihydroxyalkoxy radical; a $C_1$–$C_2$ carboxyalkoxy radical; a chlorine, bromine or fluorine atom; a $C_1$–$C_2$ trifluoroalkyl radical; a radical:

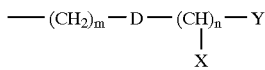

wherein m and n have the same meanings as recited above; D, X and Y have the same meanings as recited above; or a radical $NR_{10}R_{11}$, wherein $R_{10}$ and $R_{11}$ have the same meanings as recited above;

$Z_2$ represents O or $NR_{10}$, wherein R represents H, an acetyl, $C_1$–$C_4$ alkyl, $C_1$–$C_4$ hydroxyalkyl or $C_1$–$C_4$ aminoalkyl radical; it being understood that the alkyl or alkoxy radicals of the groups defined above may be linear or branched with the proviso that:

(i) when $R'_1$ represents phenyl, $R'_2$ represents methyl and $R'_3$ represents hydrogen, A' is other than 4-dimethylaminophenyl and 4-diethylaminophenyl; and (ii) when $R'_1$, $R'_2$ and $R'_3$ represent hydrogen, A' is other than the para-(2-methyl-5-aminophenol) and para-(1,3-diaminobenzene) radicals.

32. A process for preparing a compound of formula (II') as defined in claim 31, said process comprising the step of reacting, in an aqueous-alcoholic medium and at a temperature ranging from 10 to 60° C., a 4,5-diaminopyrazole of formula (3):

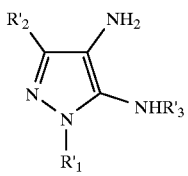

with a compound of formula (4):

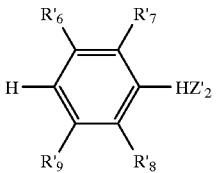

wherein $R'_1$, $R'_2$, and $R'_3$ have the same meanings as recited in claim 31, and wherein $R'_6$, $R'_7$, $R'_8$, and $R'_9$ have the same respective meanings as the radicals $R_6$, $R_7$, $R_8$ and $R_9$ recited in claim 31 and $Z'_2$ represents O or NR wherein R has the same meaning as recited in claim 31.

33. A process according to claim 32, wherein said compound of formula (4) is a compound of formula:

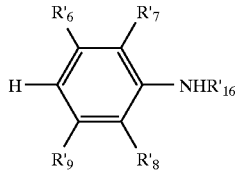

wherein $R'_6$, $R'_7$, $R'_8$ and $R'_9$ have the same meanings as recited in claim 32 and $R'_{16}$ represents hydrogen or a linear or branched $C_1$–$C_4$ alkyl.

34. A process according to claim 32, wherein said compound of formula (4) is a compound of formula:

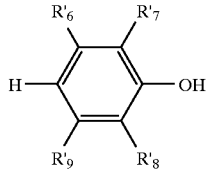

wherein $R'_6$, $R'_7$, $R'_8$ and $R'_9$ have the same meanings as recited in claim 32.

35. A dye, said dye being a 5-amino-2-methyl-N-(5-aminopyrazol-4-yl)-p-quinone monoimine or a 5-imino-4-[(2'-amino-4'-hydroxy-5'-methyl)phenyl]iminopyrazoline tautomeric form thereof.

36. A dye, said dye being a 5-amino-2-methyl-N-(5-amino-1-methylpyrazol-4-yl)-p-quinone monoimine or a 5-imino-4-[(2'-amino-4'-hydroxy-5'-methyl)phenyl]imino-1-methylpyrazoline tautomeric form thereof.

37. A dye, said dye being a 5-amino-2-methyl-N-(5-amino-1,3-dimethylpyrazol-4-yl)-p-quinone monoimine or a 5-imino-4-[(2'-amino-4'-hydroxy-5'-methyl)phenyl]imino-1,3-dimethylpyrazoline tautomeric form thereof.

38. A process for lightening keratin fibres, said process comprising the step of applying to said keratin fibres an effective amount of a composition according to claim 1, said composition further comprising an oxidizing agent which is added to said composition at the time of application, said composition having a pH above 7 at the time of application.

* * * * *